United States Patent
Toyokawa et al.

(10) Patent No.: US 9,400,429 B2
(45) Date of Patent: Jul. 26, 2016

(54) COMPOSITION FOR FORMING A RESIST UNDERLAYER FILM, AND PATTERN-FORMING METHOD

(71) Applicant: JSR CORPORATION, Tokyo (JP)

(72) Inventors: Fumihiro Toyokawa, Tokyo (JP); Shin-ya Nakafuji, Tokyo (JP); Gouji Wakamatsu, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/642,857

(22) Filed: Mar. 10, 2015

(65) Prior Publication Data

US 2015/0185613 A1 Jul. 2, 2015

Related U.S. Application Data

(63) Continuation of application No. PCT/JP2013/074164, filed on Sep. 6, 2013.

(30) Foreign Application Priority Data

Sep. 10, 2012 (JP) .................................. 2012-198837

(51) Int. Cl.
| | |
|---|---|
| *G03F 7/004* | (2006.01) |
| *G03F 7/11* | (2006.01) |
| *C07C 279/08* | (2006.01) |
| *C07C 217/18* | (2006.01) |
| *G03F 7/26* | (2006.01) |
| *G03F 7/09* | (2006.01) |
| *H01L 21/02* | (2006.01) |
| *H01L 21/027* | (2006.01) |
| *H01L 21/306* | (2006.01) |
| *H01L 21/308* | (2006.01) |
| *C08G 8/04* | (2006.01) |
| *C08G 8/20* | (2006.01) |
| *C08L 61/06* | (2006.01) |

(52) U.S. Cl.
CPC ............... *G03F 7/11* (2013.01); *C07C 217/18* (2013.01); *C07C 279/08* (2013.01); *C08G 8/04* (2013.01); *C08G 8/20* (2013.01); *C08L 61/06* (2013.01); *G03F 7/094* (2013.01); *G03F 7/26* (2013.01); *H01L 21/02057* (2013.01); *H01L 21/0274* (2013.01); *H01L 21/3081* (2013.01); *H01L 21/30604* (2013.01); *C07C 2103/92* (2013.01)

(58) Field of Classification Search
CPC ......... G03F 7/004; G03F 7/091; G03F 7/094; G03F 7/11; G03F 7/26; G03F 7/40; G03F 7/0382; H01L 21/0271; H01L 7/0274; C07C 2103/92; C07C 279/08; C07C 217/18
USPC ............. 430/270.1, 271.1, 280.1, 281.1, 322, 430/325, 329, 330, 331; 568/632, 631, 325
See application file for complete search history.

(56) References Cited

U.S. PATENT DOCUMENTS

| | | | |
|---|---|---|---|
| 4,642,362 A | 2/1987 | Harris et al. | |
| 6,380,095 B1* | 4/2002 | Liu | ...................... H01L 21/3065 257/E21.218 |
| 7,053,005 B2* | 5/2006 | Lee | ...................... C23C 18/1212 257/E21.243 |
| 7,705,189 B2* | 4/2010 | Nishikubo | ............... C07C 13/70 430/270.1 |
| 8,257,910 B1* | 9/2012 | Guerrero | .................... G03F 7/26 430/322 |
| 8,691,496 B2* | 4/2014 | Konno | .................... G03F 7/091 430/270.1 |
| 2010/0028802 A1* | 2/2010 | Konno | ..................... G03F 7/091 430/270.1 |
| 2010/0047709 A1 | 2/2010 | Echigo et al. | |
| 2010/0279227 A1* | 11/2010 | Kishioka | ................. C08G 59/40 430/280.1 |
| 2012/0171379 A1 | 7/2012 | Echigo et al. | |
| 2013/0004900 A1 | 1/2013 | Konno et al. | |
| 2013/0098870 A1* | 4/2013 | Wakamatsu | ............ B44C 1/227 216/49 |

FOREIGN PATENT DOCUMENTS

| | | |
|---|---|---|
| JP | 2000-143937 A | 5/2000 |
| JP | 2001-040293 A | 2/2001 |
| JP | 2001-215694 A | 8/2001 |
| JP | 2002-296789 A | 10/2002 |
| JP | 2004-168748 A | 6/2004 |
| JP | 2008-116677 A | 5/2008 |
| JP | 5051133 B2 | 10/2012 |
| JP | 2013-077010 A | 4/2013 |
| WO | WO 2008/038544 A1 | 4/2008 |
| WO | WO 2009/072465 A1 | 6/2009 |
| WO | WO 2012/043403 A1 | 4/2012 |

OTHER PUBLICATIONS

International Search Report issued Oct. 1, 2013 in PCT/JP2013/074164 filed Sep. 6, 2013 (w/ English translation).
Extended European Search Report issued May 23, 2016, in European Patent Application No. 13835872.6.

* cited by examiner

*Primary Examiner* — Amanda C Walke
(74) *Attorney, Agent, or Firm* — Oblon, McClelland, Maier & Neustadt, L.L.P.

(57) ABSTRACT

A composition for forming a resist underlayer film is provided, which contains: a calixarene-based compound obtained from a calixarene by substituting at least a part of hydrogen atoms each on phenolic hydroxyl groups comprised in the calixarene, with a monovalent organic group having 1 to 30 carbon atoms; and an organic solvent. The monovalent organic group preferably includes a crosslinkable group. A part of hydrogen atoms each on phenolic hydroxyl groups of the calixarene-based compound is preferably substituted. The ratio of the number of substituted phenolic hydroxyl groups to the number of unsubstituted phenolic hydroxyl groups in the calixarene-based compound is preferably no less than 30/70 and no greater than 99/1.

16 Claims, No Drawings

COMPOSITION FOR FORMING A RESIST UNDERLAYER FILM, AND PATTERN-FORMING METHOD

CROSS-REFERENCE TO RELATED APPLICATIONS

The present application is a continuation application of International Application No. PCT/JP2013/074164, filed Sep. 6, 2013, which claims priority to Japanese Patent Application No. 2012-198837, filed Sep. 10, 2012. The contents of these applications are incorporated herein by reference in their entirety.

BACKGROUND OF THE INVENTION

1. Field of the Invention

The present invention relates to a composition for forming a resist underlayer film, and a pattern-forming method.

2. Discussion of the Background

In manufacturing integrated circuit elements and the like, a pattern-forming method utilizing a multilayer resist process has been in widespread use to meet miniaturization of processing size. With respect to the multilayer resist process, in general, a composition for forming a resist underlayer film is applied on the upper side of a substrate to provide a resist underlayer film, and a resist composition is further applied on the upper side of resist underlayer film to provide a resist film. Then, a transfer of a mask pattern by way of irradiation with exposure light and a subsequent development yields a resist pattern. Subsequently, the resist pattern is transferred to the resist underlayer film by dry etching. Finally, the resist underlayer film pattern is transferred to the substrate by dry etching, whereby the substrate with a desired pattern can be obtained.

In general, materials having a high carbon content are used for the resist underlayer film provided directly on the substrate. Such a high carbon content leads to an increase of etching selectivity in the processing of the substrate, which enables more precise pattern transfer. Known compositions for forming such a resist underlayer film include: a composition that contains a thermosetting phenol novolak resin (see PCT International Publication No. 2009/072465); a composition that contains an acenaphthylene resin (see Japanese Unexamined Patent Application, Publication Nos. 2000-143937 and 2001-40293); and a composition that contains a calixarene (see Japanese Unexamined Patent Application, Publication No. 2008-116677), and these compositions can reportedly provide a resist underlayer film exhibiting superior etching resistance.

On the other hand, in these days, formation of a pattern on a substrate having a plurality of types of trenches, in particular, trenches differing from one another in terms of an aspect ratio has been executed more frequently.

SUMMARY OF THE INVENTION

According to one aspect of the present invention, a composition for forming a resist underlayer film includes a calixarene-based compound and an organic solvent. The calixarene-based compound is obtained from a calixarene by substituting at least a part of hydrogen atoms each on phenolic hydroxyl groups included in the calixarene, with a monovalent organic group having 1 to 30 carbon atoms.

According to another aspect of the present invention, a pattern-forming method includes in a following order of: providing a resist underlayer film directly or indirectly on a substrate; forming a resist pattern directly or indirectly on the resist underlayer film; forming a pattern on the substrate through dry etching of the resist underlayer film, the substrate, or both the resist underlayer film and the substrate using the resist pattern as a mask; and removing the resist underlayer film remaining on the substrate using a basic solution. The method further includes subjecting the resist underlayer film to heating or an acid treatment before removing the resist underlayer film. The resist underlayer film is provided using the composition for forming a resist underlayer film.

DESCRIPTION OF EMBODIMENTS

According to an embodiment of the invention made for solving the aforementioned problems, a composition for forming a resist underlayer film contains:

a calixarene-based compound obtained from a calixarene by substituting at least a part of hydrogen atoms each on phenolic hydroxyl groups comprised in the calixarene, with a monovalent organic group having 1 to 30 carbon atoms (hereinafter, may be also referred to as "(A) compound" or "compound (A)"); and an organic solvent (hereinafter, may be also referred to as "(B) organic solvent" or "organic solvent (B)").

According to another embodiment of the present invention, a pattern-forming method includes in the following order of:

providing a resist underlayer film directly or indirectly on a substrate;

forming a resist pattern directly or indirectly on the resist underlayer film;

forming a pattern on the substrate through dry etching of the resist underlayer film, the substrate, or both the resist underlayer film and the substrate using the resist pattern as a mask; and removing the resist underlayer film remaining on the substrate using a basic solution, wherein the method further includes subjecting the resist underlayer film to heating or an acid treatment before removing the resist underlayer film, and wherein the resist underlayer film is provided using the composition for forming a resist underlayer film according to the embodiment of the present invention.

The term "calixarene-based compound" as referred to herein means a compound obtained from a calixarene by substituting at least a part of hydrogen atoms each on phenolic hydroxyl groups included in the calixarene, with a monovalent organic group having 1 to 30 carbon atoms. The term "calixarene" as referred to means a cyclic oligomer derived from a plurality of aromatic rings to which a hydroxy group bonds, or a plurality of heteroaromatic rings to which a hydroxy group bonds, through linking to form a ring via a hydrocarbon group. The term "phenolic hydroxyl groups included in a calixarene" as referred to means all of the hydroxy groups which directly bond to the aromatic rings or the heteroaromatic rings each included in the calixarene, and includes phenolic hydroxyl groups derived from any of a phenolic compound and an aldehyde compound used in the formation of the calixarene. The term "organic group" as referred to means a group having at least one carbon atom(s).

The composition for forming a resist underlayer film according to the embodiment of the present invention enables a resist underlayer film superior in flatness, solvent resistance and outgas-inhibitory ability to be formed. The pattern-forming method according to the another embodiment of the present invention enables a resist underlayer film superior in flatness, solvent resistance and outgas-inhibitory ability to be formed, and in turn, a favorable pattern to be formed. Therefore, the composition for forming a resist underlayer film and the pattern-forming method can be suitably used for producing semiconductor devices in which further progress of miniaturization is expected in the future. Hereinafter, embodiments of the the present invention are explained in detail.

Composition for Forming Resist Underlayer Film

The composition for forming a resist underlayer film contains the compound (A) and the organic solvent (B). The composition for forming a resist underlayer film may contain a resin (hereinafter, may be also referred to as "(C) resin" or "resin (C)") as a favorable component, and may contain other optional component within a range not leading to impairment of the effects of the present invention.

The composition for forming a resist underlayer film enables a resist underlayer film superior in flatness to be formed. The composition for forming a resist underlayer film can be suitably used for, for example, a substrate having a plurality of types of trenches; even in a case where the plurality of types of trenches differ from one another in terms of an aspect ratio (for example, a ratio of the width to the depth of the trench), and further even in a case where the difference in the aspect ratio from one another is significant, or for example, the ratio of the maximum value to the minimum value of the aspect ratios is no less than 10, the composition for forming a resist underlayer film can be suitably used, and a resist underlayer film superior in flatness can be formed. Such a substrate having a plurality of types of trenches is exemplified by a $SiO_2$ stepped substrate in which one or two or more types of trenches having a width of 20 nm to 300 nm, a pitch of 1.2 to 5 times the width, and a depth of 20 nm to 300 nm; trenches having a width of 0.3 μm to 10 μm, and a depth of 20 nm to 300 nm (open spaces), and the like are provided in combination; and the like. Moreover, according to the composition for forming a resist underlayer film, the resist underlayer film formed also has superior solvent resistance and outgas inhibitory ability. Furthermore, the composition for forming a resist underlayer film can be applied on silicon wafers of a size of 450 mm or the like with superior intraplane uniformity.

Although not necessarily clarified, the reason for achieving the above-described effects due to the composition for forming a resist underlayer film having the constitution described above is presumed as in the following, for example. Specifically, since the compound (A) has an appropriate and substantially uniform molecular weight, and the hydrogen atom of a part or all of the phenolic hydroxyl groups are substituted with the monovalent organic group, the compound (A) exhibits moderate sublimability, with improved insolubility in a solvent contained in typical resist compositions, as well as improved solubility in a solvent contained in the composition for forming a resist underlayer, and further the viscosity of the composition for forming a resist underlayer film is decreased appropriately. As a result, the composition for forming a resist underlayer can be suitably used for a material for an underlayer to be coated, and enables a resist underlayer film superior in flatness, solvent resistance and outgas-inhibitory ability to be formed.

Hereinafter, each component will be explained.

(A) Compound

The compound (A) is a compound obtained from a calixarene by substituting at least a part of hydrogen atoms each on phenolic hydroxyl groups included in the calixarene, with a monovalent organic group having 1 to 30 carbon atoms. Due to containing the compound (A), the composition for forming a resist underlayer film can provide a resist underlayer film superior in flatness, solvent resistance and outgas-inhibitory ability. The composition for forming a resist underlayer film may contain one, or two or more types of the compound (A).

The monovalent organic group having 1 to 30 carbon atoms is exemplified by: a monovalent hydrocarbon group; a group that includes a hetero atom-containing group between two carbon atoms in the monovalent hydrocarbon group; a group obtained by substituting a part or all of hydrogen atoms included in any one of these groups with a substituent; and the like.

The monovalent hydrocarbon group is exemplified by a monovalent chain hydrocarbon group having 1 to 30 carbon atoms, a monovalent alicyclic hydrocarbon group having 3 to 30 carbon atoms, a monovalent aromatic hydrocarbon group having 6 to 30 carbon atoms, and the like.

Examples of the monovalent chain hydrocarbon group include:

alkyl groups such as a methyl group, an ethyl group, a propyl group, a butyl group and a pentyl group;

alkenyl groups such as an ethenyl group, a propenyl group, a butenyl group and a pentenyl group;

alkynyl groups such as an ethynyl group, a propynyl group, a butynyl group and a pentynyl group; and the like.

Examples of the monovalent alicyclic hydrocarbon group include:

monocyclic cycloalkyl groups such as a cyclopropyl group, a cyclobutyl group, a cyclopentyl group and a cyclohexyl group;

monocyclic unsaturated alicyclic hydrocarbon groups such as a cyclopropenyl group, a cyclobutenyl group, a cyclopentenyl group, a cyclohexenyl group and a cyclopentanedienyl group;

polycyclic cycloalkyl groups such as a norbornyl group, an adamantyl group, a tricyclodecyl group and a tetracyclododecyl group;

polycyclic unsaturated alicyclic hydrocarbon groups such as a norbornenyl group, a tricyclodecenyl group, a tetracyclododecyl group and a norbornanedienyl group; and the like.

Examples of the monovalent aromatic hydrocarbon group include:

aryl groups such as a phenyl group, a tolyl group, a xylyl group, a mesityl group, a naphthyl group, a methylnaphthyl group, an anthryl group and a methylanthryl group;

aralkyl groups such as a benzyl group, a phenethyl group, a naphthylmethyl group and an anthrylmethyl group; and the like.

Examples of the hetero atom-containing group include —O—, —S—, —NR'—, —CO—, —CS—, groups obtained by combining two or more of these groups; and the like, wherein R' represents a monovalent hydrocarbon group having 1 to 10 carbon atoms.

Examples of the group that includes a hetero atom-containing group between two carbon atoms in the monovalent hydrocarbon group include:

chain groups including for example, alkoxyalkyl groups, alkylsulfanylalkyl groups, alkyliminoalkyl groups, acylalkyl groups, alkylthiocarbonylalkyl groups; and cyclic groups including for example, cyclic ether groups, cyclic thioether groups, cyclic amino groups, cyclic ketone groups, cyclic thioketone groups.

Examples of the substituent include: halogen atoms such as a fluorine atom, a chlorine atom, a bromine atom and an iodine atom; a hydroxy group; a carboxy group; a cyano group; a nitro group; alkoxy groups; alkoxycarbonyl groups; alkoxycarbonyloxy groups; acyl groups; acyloxy groups; and the like.

The monovalent organic group preferably includes a crosslinkable group. When the monovalent organic group includes the crosslinkable group, the strength of the resist underlayer film formed can be increased, and organic solvent resistance can be improved owing to crosslinking between the compounds (A) or between the compound (A) and the resin (C) described later. The term "crosslinkable group" as referred to means a group capable of forming a covalent bond between identical or different molecules.

Examples of the crosslinkable group include groups include: groups including a polymerizable carbon-carbon double bond; groups including a polymerizable carbon-carbon triple bond; an epoxy group; alkoxymethyl groups; a formyl group; an acetyl group; dialkylaminomethyl groups; a dimethylolaminomethyl group; and the like. Of these, groups including a polymerizable carbon-carbon double bond are preferred, and a vinyl group, a vinylphenyl group, and a (meth)acryloyl group are preferred.

Examples of the monovalent organic group including the crosslinkable group include groups represented by the following formulae (a) to (c), and the like.

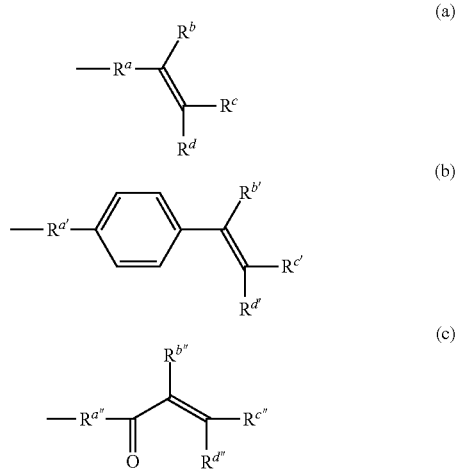

In the above formulae (a) to (c), $R^a$ and $R^{a'}$ each independently represent a single bond or an alkanediyl group having 1 to 10 carbon atoms; $R^{a''}$ represents a single bond, an alkanediyl group, a hydroxyalkanediyloxy group or $(R''O)_i$; R'' represents an alkanediyl group; "i" is an integer of 1 to 10; and $R^b$, $R^{b'}$, $R^{b''}$, $R^c$, $R^{c'}$, $R^{c''}$, $R^d$, $R^{d'}$ and $R^{d''}$ each independently represent a hydrogen atom or a monovalent hydrocarbon group.

Preferably "i" is an integer of 1 to 4, more preferably 1 to 3, and still more preferably 1 or 2.

Examples of the alkanediyl group which may be represented by $R^a$, $R^{a'}$ and $R^{a''}$ include an ethanediyl group, a propanediyl group, a butanediyl group, and the like.

Examples of the hydroxyalkanediyloxy group which may be represented by $R^{a''}$ include a 2-hydroxypropanediyloxy group, a 2-hydroxybutanediyloxy group, and the like.

Examples of $(R''O)_i$ which may be represented by $R^{a''}$ include an oxyethanediyl group, an oxypropanediyl group, an oxybutanediyl group, an oxyethanediyloxyethanediyl group, an oxypropanediyloxypropanediyl group, an oxybutanediyloxybutanediyl group, and the like.

Examples of the monovalent organic group represented by the above formula (a) include a vinyl group, an allyl group, a 3-butenyl group, a 2-methyl-2-propenyl group, a 3-methyl-2-propenyl group, and the like.

Examples of the monovalent organic group represented by the above formula (b) include a 4-vinylbenzyl group, a 4-vinylphenyl group, a 2-vinylbenzyl group, a 4-allylbenzyl group, and the like.

Examples of the monovalent organic group represented by the above formula (c) include a (meth)acryloyl group, a (meth)acryloyloxyethyl group, a (meth)acryloyloxyethoxyethyl group, a (meth)acryloyloxy-2-hydroxypropyl group, a (meth)acryloyloxypropyl group, a (meth)acryloyloxybutyl group, and the like.

Of these, the monovalent organic group is preferably a vinyl group, an allyl group, a 2-methyl-2-propenyl group, a 3-methyl-2-propenyl group, a 4-vinylbenzyl group, a 4-vinylphenyl group, a (meth)acryloyl group, a (meth)acryloyloxyethyl group, a (meth)acryloyloxyethoxyethyl group, or a (meth)acryloyloxy-2-hydroxypropyl group.

As the monovalent organic group, a group that does not substantially include a crosslinkable group is also preferred. Due to the monovalent organic group not substantially including a crosslinkable group, film shrinkage that occurs in the formation of the resist underlayer film can be inhibited, and as a result, the flatness of the resist underlayer film formed can be improved.

Examples of the monovalent organic group that does not include a crosslinkable group include:

alkyl groups such as an ethyl group, a propyl group and a butyl group;

cycloalkyl groups such as a cyclopentyl group, a cyclohexyl group, a cycloheptyl group, a cyclooctyl group, a norbornyl group and an adamantyl group;

aromatic hydrocarbon groups such as a phenyl group, a tolyl group, a xylyl group, a mesityl group, a benzyl group, a phenethyl group, a naphthyl group, a 1-naphthylmethyl group, a 2-naphthylmethyl group, a 1-naphthylethyl group, a 2-naphthylethyl group, an anthryl group and a 2-anthrylmethyl group;

hydroxy group-containing alkyl groups such as a 2,3-dihydroxypropyl group, a 3-phenoxy-2-hydroxypropyl group and a 2,3-dihydroxybutyl group;

alkoxycarbonyl-containing groups such as a t-butoxycarbonylmethyl group, a t-butoxycarbonyl group, a t-pentyloxycarbonylmethyl group and a t-pentyloxycarbonyl group; and the like.

Of these, cycloalkyl groups, aromatic hydrocarbon groups, hydroxy group-containing alkyl groups, and alkoxycarbonyl-containing groups are preferred, and a cyclopentyl group, a cyclohexyl group, a benzyl group, a 2-naphthylmethyl group, a 2,3-dihydroxypropyl group, a 3-phenoxy-2-hydroxypropyl group, a t-butoxycarbonylmethyl group, and a t-butoxycarbonyl group are more preferred.

Moreover, a monovalent organic group that can be eliminated upon a baking treatment, an acid treatment or the like is also preferred as the monovalent organic group. When the monovalent organic group that can be eliminated upon a baking treatment, an acid treatment or the like is selected as a substituent of the phenolic hydroxyl group, the resist underlayer film remaining after the pattern formation can be removed using a basic solution. In such a case, the resist film can be removed without employing an ashing treatment or the like, and thus, the influence of the ashing treatment or the like on the substrate can be minimized.

It is preferred that a part of hydrogen atoms each on phenolic hydroxyl groups of the compound (A) is substituted. In the compound (A), when a part of hydrogen atoms each on phenolic hydroxyl groups included in a calixarene is substituted, the compound (A) includes at least one phenolic hydroxyl group(s). Accordingly, the wettability of the composition for forming a resist underlayer film on a substrate can be improved, and as a result, adhesiveness of the formed resist underlayer film to a substrate can be improved.

The ratio of the number of substituted phenolic hydroxyl groups to the number of unsubstituted phenolic hydroxyl groups (the number of substituted phenolic hydroxyl group/ the number of unsubstituted phenolic hydroxyl group) in the compound (A) is preferably no less than 30/70 and no greater than 99/1, more preferably no less than 40/60 and no greater than 95/5, still more preferably no less than 50/50 and no greater than 90/10, and particularly preferably no less than 60/40 and no greater than 85/15. The term "substituted phenolic hydroxyl group" as referred to means a phenolic hydroxyl group whose hydrogen atom is substituted with a monovalent organic group having 1 to 30 carbon atoms. When the number ratio falls within the above range, the solubility of the compound (A) in the organic solvent (B) can be increased, and the wettability of the compound (A) on a substrate can be further increased. As a result, the adhesiveness of the resist underlayer film formed from the composition for forming a resist underlayer film to a substrate can be further improved. In a case where the composition for forming a resist underlayer film contains a plurality of types of compound (A), the number ratio means a ratio of the number of substituted phenolic hydroxyl groups to the number of unsubstituted phenolic hydroxyl groups each included in a certain mass of mixture constituted with the plurality of types of compound (A).

It is to be noted that the number ratio can be calculated based on a'H-NMR measurement of the compound (A). The calculation method may be appropriately selected according to the structure and/or synthesis method of the calixarene-based compound. Examples of the calculation method include: a method in which the number ratio is calculated from an area of a peak derived from hydrogen atoms on aromatic rings to which an unsubstituted phenolic hydroxyl group bonds and an area of a peak derived from hydrogen atoms on aromatic rings to which a substituted phenolic hydroxyl group bonds; a method in which the number ratio is calculated from a ratio of an area of a peak derived from hydrogen atoms included in unsubstituted phenolic hydroxyl groups, an area of a peak derived from hydrogen atoms included in calixarene-based compounds, and an area of a peak derived from hydrogen atoms included in substituents on substituted phenolic hydroxyl groups; and the like.

The compound (A) is preferably derived from a compound obtained by subjecting a compound represented by the following formula (1) and a compound represented by the following formula (2) to a condensation reaction. In this instance, the compound (A) can be obtained by subjecting a hydroxy compound represented by the following formula (1) and an aldehyde compound represented by the following formula (2) to a condensation reaction to obtain a calixarene, and substituting the hydrogen atom of phenolic hydroxyl groups included in the calixarene with a monovalent organic group having 1 to 30 carbon atoms.

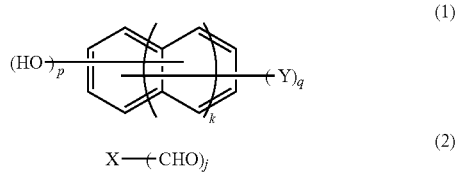

(1)

X—(CHO)$_j$ (2)

In the above formula (1), Y represents a hydrocarbon group having 1 to 10 carbon atoms; q is an integer of 0 to 7; p is an integer of 1 to 3, wherein a sum of p and q is no less than 1 and no greater than 8; and k is 0 or 1, wherein in a case where q is no less than 2, a plurality of Ys are identical or different.

In the above formula (2), X represents a substituted or unsubstituted hydrocarbon group having 1 to 30 carbon atoms and having a valency of j, or hydrogen atom; and j is 1 or 2.

The hydrocarbon group having 1 to 10 carbon atoms represented by Y is exemplified by hydrocarbon groups having 1 to 10 carbon atoms among the hydrocarbon groups exemplified as the monovalent organic group, and the like.

Of these, hydrocarbon groups having 1 to 5 carbon atoms are preferred, alkyl groups having 1 to 5 carbon atoms are more preferred, a propyl group and a butyl group are still more preferred, and a t-butyl group is particularly preferred.

In a case where k is 0, p is preferably 2 or 3, and in a case where k is 1, p is preferably 1.

Preferably q is an integer of 0 to 2, more preferably 0 or 1, and still more preferably 0.

The substituted or unsubstituted hydrocarbon group having 1 to 30 carbon atoms and having a valency of j which may be represented by X is exemplified by: substituted or unsubstituted hydrocarbon group having 1 to 30 carbon atoms among substituted or unsubstituted hydrocarbon groups exemplified as the monovalent organic group, and the like in a case where j is 1; and groups obtained by eliminating one hydrogen atom from the group described above, and the like in a case where j is 2.

Preferably j is 1.

X represents preferably a hydrogen atom, a substituted or unsubstituted chain hydrocarbon group, or a substituted or unsubstituted aromatic hydrocarbon group, more preferably a hydrogen atom, a substituted or unsubstituted divalent chain hydrocarbon group, or a substituted or unsubstituted monovalent aromatic hydrocarbon group, still more preferably a hydrogen atom, an alkylene group, a hydroxy substituted phenyl group, or an unsubstituted naphthyl group, and particularly preferably a hydrogen atom, a trimethylene group, a 4-hydroxyphenyl group, a 3,4-dihydroxyphenyl group, a 3,4, 5-trihydroxyphenyl group, or a 2-naphthyl group.

The compound (A) is preferably a compound represented by the following formula (3), a compound represented by the following formula (4), or a compound represented by the following formula (5).

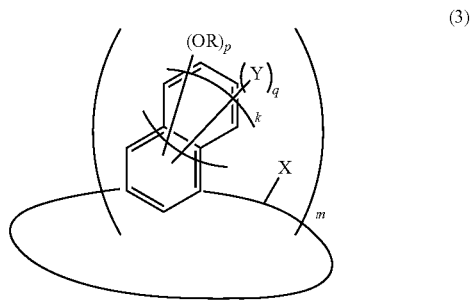

In the above formula (3), R represents a hydrogen atom or a monovalent organic group having 1 to 30 carbon atoms; m is an integer of 4 to 12; Y, k, p and q are as defined in the above formula (1); and X is as defined in the case where j in the above formula (2) is 1, wherein a plurality of Rs are identical or different, a plurality of Xs are identical or different, a plurality of "k"s are identical or different, a plurality of "p"s are identical or different, and a plurality of "q"s are identical or different, and wherein in a case where Y is present in a plurality of number, a plurality of Ys are identical or different.

The lower limit of m is preferably 4, and more preferably 5 in light of an improvement of the outgas inhibitory ability of the resist underlayer film formed from the composition for forming a resist underlayer film. The upper limit of m is preferably 8, more preferably 7, and still more preferably 6 in light of an improvement of burying performances of the composition for forming a resist underlayer film.

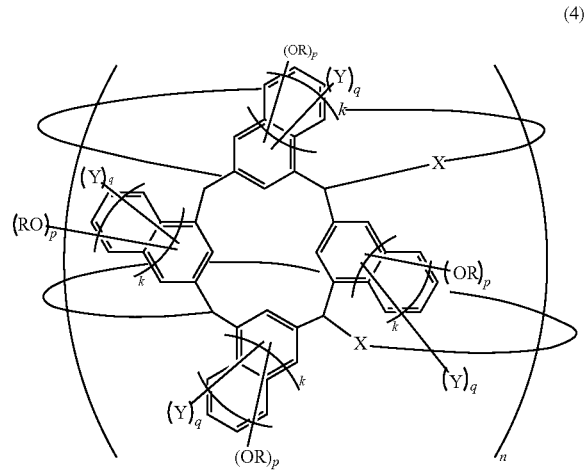

(4)

In the above formula (4), R represents a hydrogen atom or a monovalent organic group having 1 to 30 carbon atoms; n is 2 or 3; Y, k, p and q are as defined in the above formula (1); and X is as defined in the case where j in the above formula (2) is 2, wherein a plurality of Rs are identical or different, a plurality of Xs are identical or different, a plurality of "k"s are identical or different, a plurality of "p"s are identical or different, and a plurality of "q"s are identical or different, and wherein in a case where Y is present in a plurality of number, a plurality of Ys are identical or different.

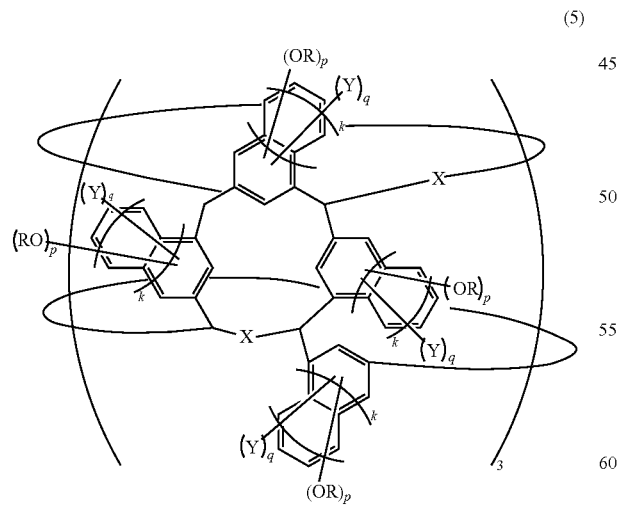

(5)

In the above formula (5), R represents a hydrogen atom or a monovalent organic group having 1 to 30 carbon atoms; Y, k, p and q are as defined in the above formula (1); and X is as defined in the case where j in the above formula (2) is 2, wherein a plurality of Rs are identical or different, a plurality of Xs are identical or different, a plurality of "k"s are identical or different, a plurality of "p"s are identical or different, and a plurality of "q"s are identical or different, and wherein in a case where Y is present in a plurality of number, a plurality of Ys are identical or different.

Examples of the compound (A) include compounds represented by the following formulae, and the like.

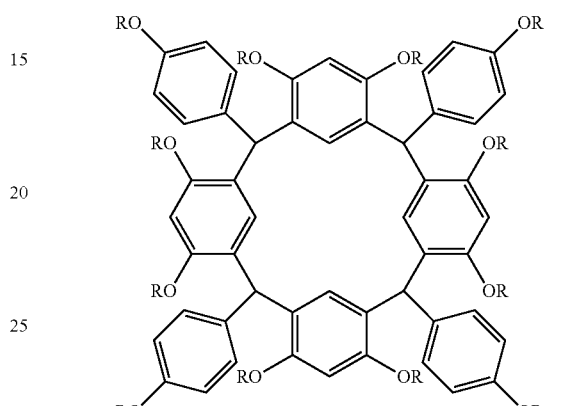

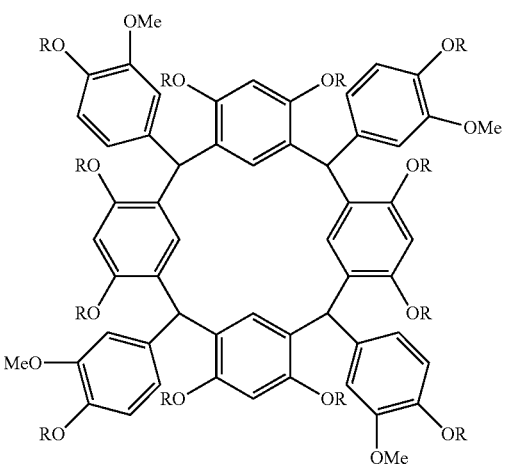

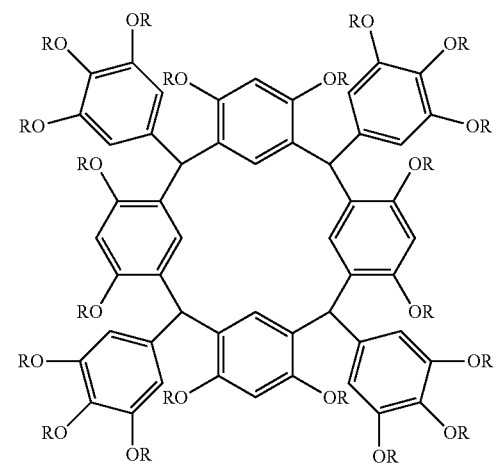

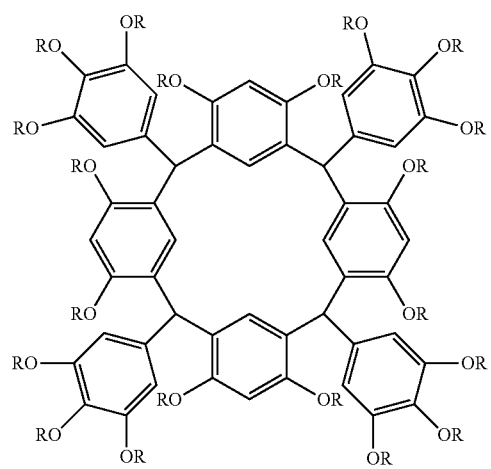

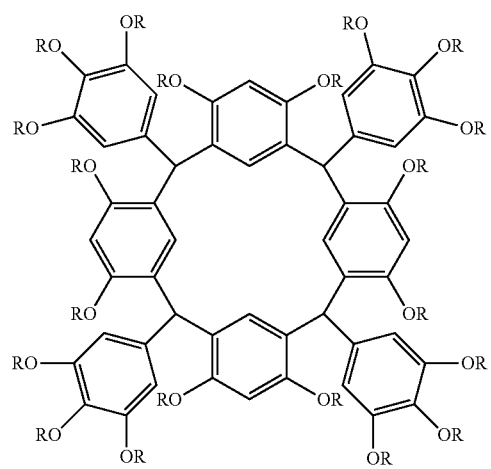

-continued
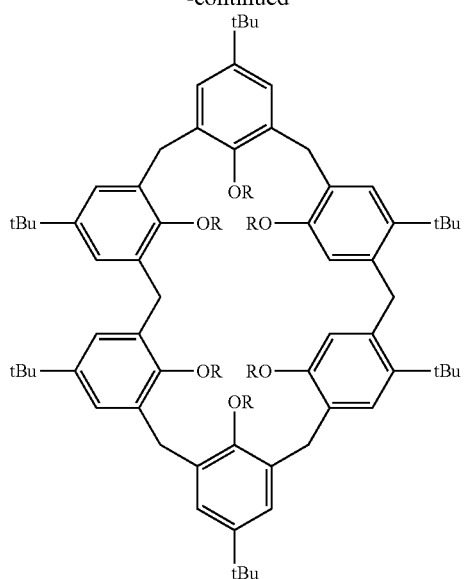
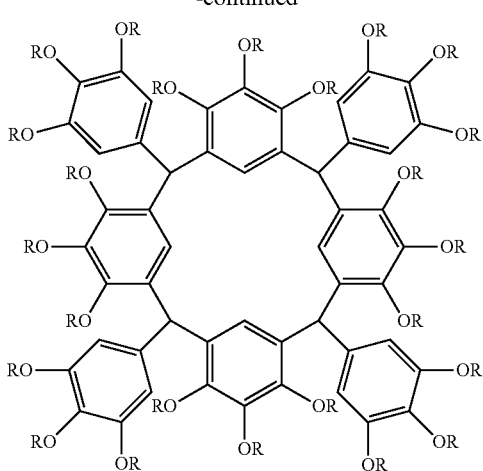
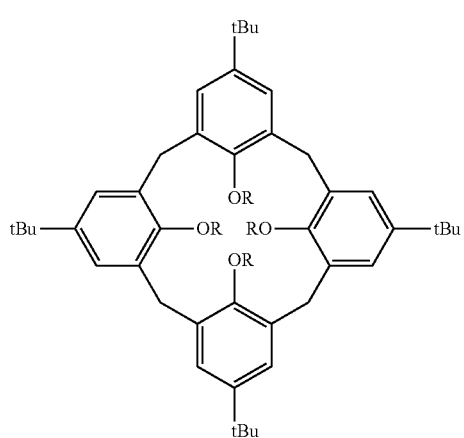
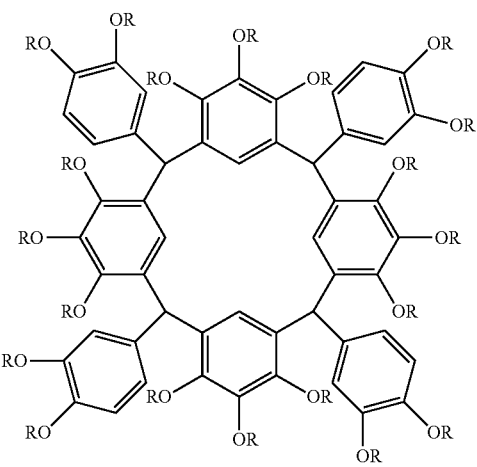
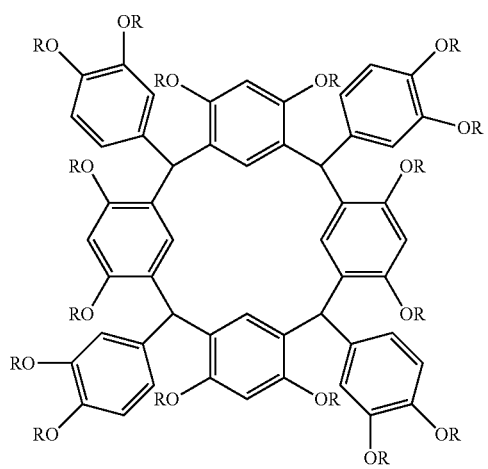

-continued

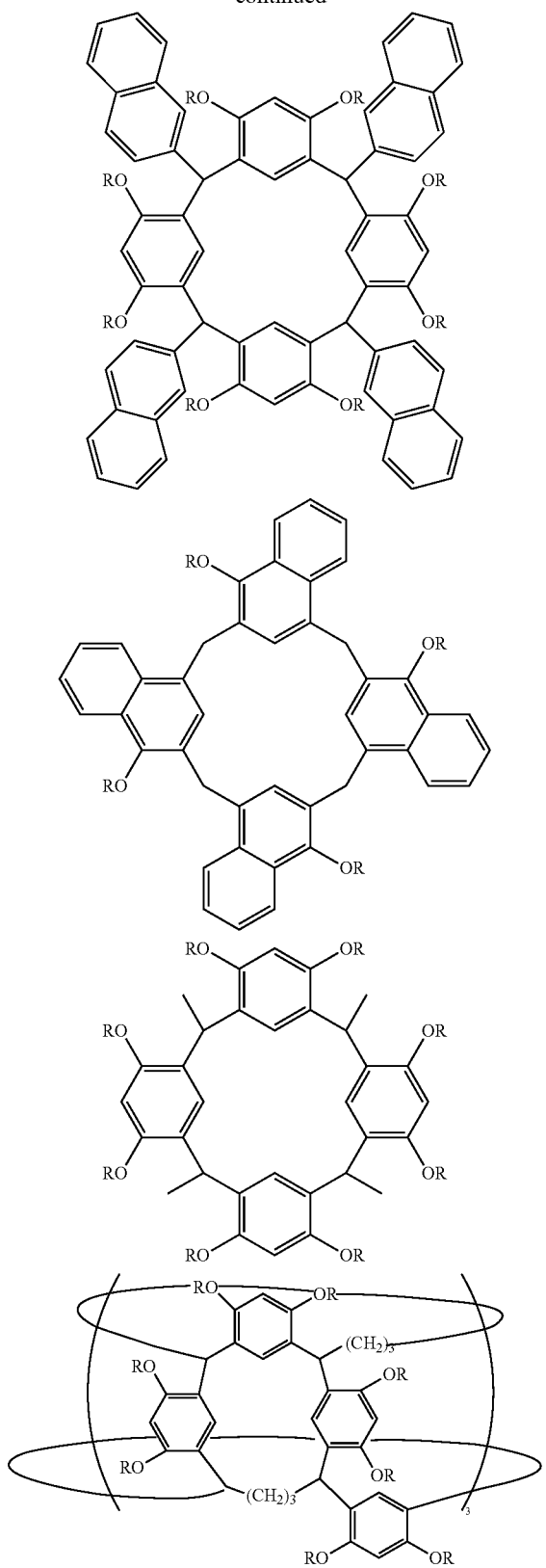

In the above formulae, Rs each independently represent a hydrogen atom or a monovalent organic group having 1 to 30 carbon atoms.

The lower limit of the molecular weight of the compound (A) is preferably 500, more preferably 700, and still more preferably 1,000 in light of an improvement of the flatness and the outgas inhibitory ability of the resist underlayer film formed. The upper limit of the molecular weight of the compound (A) is preferably 3,000, more preferably 2,500, and still more preferably 2,200 in light of an improvement of the burying performances of the composition for forming a resist underlayer film and an improvement of the flatness of the resist underlayer film.

The content of the compound (A) in the composition for forming a resist underlayer film with respect to the total solid content is preferably no less than 80% by mass, more preferably no less than 90% by mass, and still more preferably no less than 95% by mass.

(B) Organic Solvent

The organic solvent (B) is not particularly limited as long as it can dissolve or disperse the compound (A), and the optional component(s) contained as desired.

The organic solvent (B) is exemplified by an alcohol solvent, an ether solvent, a ketone organic solvent, an amide solvent, an ester organic solvent, a hydrocarbon solvent, and the like.

Examples of the alcohol solvent include monohydric alcohol solvents having 1 to 18 carbon atoms, polyhydric alcohol solvents having 2 to 18 carbon atoms, polyhydric alcohol partial ether solvents having 3 to 19 carbon atoms, and the like.

Examples of the ether solvent include:
dialkyl ether solvents such as diethyl ether, dipropyl ether and dibutyl ether;
cyclic ether solvents such as tetrahydrofuran and tetrahydropyran;
aromatic ring-containing ether solvents such as diphenyl ether and anisole; and the like.

Examples of the ketone solvent include:
chain ketone solvents such as acetone, methyl ethyl ketone, methyl n-propyl ketone, methyl n-butyl ketone, diethyl ketone, methyl iso-butyl ketone, methyl n-pentyl ketone, ethyl n-butyl ketone, methyl n-hexyl ketone, di-iso-butyl ketone and trimethylnonanone;
cyclic ketone solvents such as cyclopentanone, cyclohexanone, cycloheptanone, cyclooctanone and methylcyclohexanone;
2,4-pentanedione, acetonyl acetone and acetophenone; and the like.

Examples of the amide solvent include:
cyclic amide solvents such as N,N'-dimethylimidazolidinone and N-methylpyrrolidone;
chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include: carboxylic acid ester solvents such as monocarboxylic acid ester solvents, e.g., ethyl acetate and ethyl lactate, and polyhydric carboxylic acid ester solvents, e.g., diethyl malonate and diethyl phthalate; polyhydric alcohol partially etherified carboxylate solvents such as polyhydric alcohol partial ether acetate solvent, e.g., propylene glycol monomethyl ether acetate; lactone solvents such as butyrolactone and valerolactone; carbonate solvents such as diethyl carbonate, ethylene carbonate and propylene carbonate; and the like.

Examples of the hydrocarbon solvent include aliphatic hydrocarbon solvents having 5 to 12 carbon atoms, aromatic hydrocarbon solvents having 6 to 16 carbon atoms, and the like.

Of these, an ester solvent and a ketone solvent are preferred, a polyhydric alcohol partially etherified carboxylate solvent, a carboxylic acid ester solvent and a ketone solvent are more preferred, a polyhydric alcohol partial ether acetate solvent, a monocarboxylic acid ester solvent and a cyclic ketone solvent are still more preferred, propylene glycol monomethyl ether acetate, ethyl lactate and cyclohexanone are particularly preferred, and propylene glycol monomethyl ether acetate is more particularly preferred. The composition for forming a resist underlayer film may contain one, or two or more types of the organic solvent (B).

(C) Resin

The composition for forming a resist underlayer film may contain the resin (C) (except for those corresponding to the calixarene-based compound (A)). When the composition for forming a resist underlayer film contains the resin (C), the resist underlayer film formed from the composition for forming a resist underlayer film may exhibit improved resistance to an organic solvent contained in a composition for forming a resist film, an interlayer or the like to be provided directly or indirectly on the resist underlayer film.

Although the resin (C) is not particularly limited as long as it is a polymer compound, at least one selected from the group consisting of a novolak resin, a resol resin, a styrene resin, an acenaphthylene resin, and a polyarylene resin is/are preferred. When the resin described above is used as the resin (C), the refractive index and the extinction coefficient of the resist underlayer film can be controlled so as to give an appropriate value. As a result, the rectangularity of the cross-sectional shape of the formed resist pattern may be improved. The composition for forming a resist underlayer film may one, or two or more types of the resin (C).

The novolak resin is exemplified by a resin obtained by reacting one, or two or more of phenolic compound(s) selected from the group consisting of: phenols such as phenol, cresol, xylenol, resorcinol, bisphenol A, p-tert-butylphenol and p-octylphenol; naphthols such as α-naphthol, β-naphthol, 1,5-dihydroxynaphthalene and 2,7-dihydroxynaphthalene with an aldehyde or a divinyl compound using an acidic catalyst or the like.

The aldehyde is exemplified by: aldehydes such as formaldehyde; aldehyde sources such as paraformaldehyde and trioxane; and the like.

The divinyl compound is exemplified by divinylbenzene, dicyclopentadiene, tetrahydroindene, 4-vinylcyclohexene, 5-vinylnorborn-2-ene, α-pinene, β-pinene, limonene, 5-vinylnorbornadiene, and the like.

The resol resin is exemplified by: a resin obtained by reacting the phenolic compound with the aldehyde using an alkaline catalyst; and the like.

The styrene resin is exemplified by polystyrene; styrene copolymers such as styrene-α-methylstyrene copolymer and styrene-butadiene copolymer; and the like.

The acenaphthylene resin is exemplified by: a resin obtained by polymerizing a compound having an acenaphthylene skeleton through radical polymerization, anionic polymerization, cationic polymerization or the like, in an appropriate polymerization system such as bulk polymerization and solution polymerization; and the like. In addition, the acenaphthylene resin can be obtained by, for example, reacting a polymer of a compound having an acenaphthylene skeleton with paraformaldehyde under an acidic condition, as described in paragraphs [0008] to [0031] of Japanese Unexamined Patent Application, Publication No. 2002-296789.

The polyarylene resin is exemplified by polyarylene ether, polyarylene sulfide, polyarylene ether sulfone, polyarylene ether ketone, and the like.

The resin (C) preferably includes a naphthalene ring. When the resin (C) has the naphthalene skeleton, the refractive index and the extinction coefficient of the resist underlayer film can be controlled so as to give a more appropriate value, and as a result, the rectangularity of the cross-sectional shape of the formed resist pattern may be further improved. In addition, the resin (C) preferably includes a group including a carbon-carbon triple bond. When the resin (C) includes the above-described group, etching resistance and flexural resistance of the resist underlayer film formed may be improved. Examples of the group having a carbon-carbon triple bond include an ethynyl group, a propargyl group, and the like.

The resin (C) preferably includes a crosslinkable group. When the resin (C) includes the crosslinkable group, the strength of the resist underlayer film formed can be improved owing to the crosslinking between the resins (C) or between the resin (C) and the compound (A).

It is also preferred that the resin (C) does not substantially include a crosslinkable group. When the resin (C) does not substantially include the crosslinkable group, film shrinkage that occurs in the formation of the resist underlayer film can be inhibited, and as a result, the flatness of the resist underlayer film formed can be improved.

The weight average molecular weight (Mw) of the resin (C) is preferably no less than 2,000 and no greater than 8,000, and more preferably no less than 3,000 and no greater than 7,000. When the Mw of the resin (C) falls within the above range, the solvent resistance of the resist underlayer film formed from the composition for forming a resist underlayer film can be further improved.

The ratio (Mw/Mn) of the weight average molecular weight to the number average molecular weight (Mn) of the resin (C) is preferably 1 to 5, more preferably 1 to 3, and still more preferably 1 to 2.5.

The content of the resin (C) with respect to 100 parts by mass of the compound (A) is preferably no less than 5 parts by mass and no greater than 1,000 parts by mass, more preferably no less than 10 parts by mass and no greater than 700 parts by mass, and still more preferably no less than 30 parts by mass and no greater than 400 parts by mass. When the content of the resin (C) falls within the above range, the solvent resistance of the resist underlayer film formed from the composition for forming a resist underlayer film can be further improved.

Other Optional Component

The composition for forming a resist underlayer film may contain other optional component(s) in addition to the components (A) to (C). The other optional component is exemplified by an acid generating agent, a crosslinking agent, a surfactant, and the like. These other optional components each may be used either alone, or in combination of two or more types thereof.

Acid Generating Agent

The acid generating agent is a component that generates an acid upon an exposure or heating. When the composition for forming a resist underlayer film contains the acid generating agent, a crosslinking reaction between the compounds (A), between the compounds (C) or between the compounds (A) and the resin (C) can be allowed to proceed at comparatively low temperatures including normal temperatures.

An acid generating agent that generates an acid upon an exposure (hereinafter, may be also referred to as "photoacid generating agent") is exemplified by those described in paragraphs [0077] to [0081] of the Japanese Unexamined Patent Application, Publication No. 2004-168748.

Moreover, an acid generating agent that generates an acid upon heating (hereinafter, may be also referred to as "thermal acid generating agent") is exemplified by 2,4,4,6-tetrabromocyclohexadienone, benzoin tosylate, 2-nitrobenzyl tosylate, alkylsulfonates, and the like in addition to the onium salt acid generating agents exemplified as the photoacid generating agent described above.

Of these acid generating agents, thermal acid generating agents are preferred, onium salt acid generating agents are more preferred, iodonium salt acid generating agents are still more preferred, diphenyliodonium trifluoromethanesulfonate, diphenyliodonium nonafluoro-n-butanesulfonate, diphenyliodonium pyrenesulfonate, diphenyliodonium n-dodecylbenzenesulfonate, diphenyliodonium 10-camphorsulfonate, diphenyliodonium naphthalenesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium n-dodecylbenzenesulfonate, bis(4-t-butylphenyl)iodonium 10-camphorsulfonate and bis(4-t-butylphenyl)iodonium naphthalenesulfonate are particularly preferred, and bis(4-t-butylphenyl)iodonium nonafluoro-n-butanesulfonate is more particularly preferred.

The content of the acid generating agent with respect to 100 parts by mass of the compound (A) is preferably no greater than 5,000 parts by mass, more preferably 0.1 parts by mass to 1,000 parts by mass, and still more preferably 10 parts by mass to 300 parts by mass. One, or two or more types of the acid generating agent may be used. Moreover, the photoacid generating agent and the thermal acid generating agent may be used in combination as the acid generating agent.

Crosslinking Agent

The crosslinking agent is a compound that includes a crosslinkable group (except for those corresponding to the compound (A) and the resin (C)). When the composition for forming a resist underlayer film contains the crosslinking agent, the crosslinking between the compounds (A), between the compounds (C) or between the compounds (A) and the resin (C) can be achieved more effectively.

The crosslinking agent preferably includes two or more crosslinkable groups.

Examples of the crosslinking agent include: methoxymethylated melamines such as hexakis(methoxymethyl)melamine; methoxymethylated glycolurils such as tetrakis(methoxymethyl)glycoluril; and the like. Of these, methoxymethylated glycolurils are preferred, and 1,3,4,6-tetrakis(methoxymethyl)glycoluril is more preferred.

The content of the crosslinking agent with respect to 100 parts by mass of the compound (A) is preferably no greater than 1,000 parts by mass, more preferably 5 parts by mass to 700 parts by mass, and still more preferably 30 parts by mass to 500 parts by mass. One or two or more types of the crosslinking agent may be used.

Surfactant

The surfactant is a component that exhibits the effects of improving application properties, striation, wettability, developability and the like. The content of the surfactant with respect to 100 parts by mass of the compound (A) is preferably no greater than 15 parts by mass, and more preferably no greater than 10 parts by mass. One or two or more types of the surfactant may be used.

Preparation Method of Composition for Forming Resist Underlayer Film

The composition for forming a resist underlayer film may be prepared, for example, by mixing the compound (A) and the organic solvent (B), as well as the optional component(s) which may be contained as needed at a predetermined ratio. The composition for forming a resist underlayer film is preferably filtered through a filter of about 0.1 μm, for example, after the mixing. The solid content concentration of the composition for forming a resist underlayer film is preferably 0.1% by mass to 50% by mass, more preferably 0.5% by mass to 30% by mass, and still more preferably 1% by mass to 20% by mass. The concentration of the compound (A) in the composition for forming a resist underlayer film is preferably 0.1% by mass to 30% by mass, more preferably 0.5% by mass to 20% by mass, and still more preferably 1% by mass to 15% by mass.

The viscosity of the composition for forming a resist underlayer film at a solid content concentration of 20% by mass is preferably no less than 1 cps and no greater than 5 cps, and more preferably no less than 1 cps and no greater than 3 cps. When the value of the viscosity of the composition for forming a resist underlayer film falls within the above range, burying performances may be improved, and the flatness of the resist underlayer film formed may be improved.

Pattern-Forming Method

A pattern-forming method according another embodiment of the present invention includes in the following order of:

providing a resist underlayer film directly or indirectly on a substrate (hereinafter, may be also referred to as "resist underlayer film-providing step");

forming a resist pattern directly or indirectly on the resist underlayer film (hereinafter, may be also referred to as "resist pattern-forming step");

forming a pattern on the substrate through dry etching of the resist underlayer film, the substrate, or both the resist underlayer film and the substrate using the resist pattern as a mask (hereinafter, may be also referred to as "substrate pattern-forming step"); and removing the resist underlayer film remaining on the substrate using a basic solution (hereinafter, may be also referred to as "removing step"), wherein the method further includes the step of subjecting the resist underlayer film to heating or an acid treatment before the removing step, and wherein the resist underlayer film is provided using the composition for forming a resist underlayer film according to the embodiment of the present invention.

The substrate is preferably stepped.

Moreover, the pattern-forming method preferably includes after the resist underlayer film-providing step and before the resist pattern-forming step:

providing an intermediate layer directly or indirectly on the resist underlayer film (hereinafter, may be also referred to as "intermediate layer-providing step"), and the intermediate layer is preferably further dry etched in the substrate pattern-forming step.

According to the pattern-forming method, due to using the composition for forming a resist underlayer film described above, a resist underlayer film superior in flatness, solvent resistance and outgas-inhibitory ability can be formed, and in turn, a favorable pattern can be formed. In addition, the pattern-forming method can be also suitably applied to stepped substrates and substrates having a plurality of types of trenches; on such substrates, a resist underlayer film superior in flatness can be formed, and in turn, a favorable pattern can be formed.

Moreover, according to the pattern-forming method, since the resist underlayer film is removed with a basic solution after the formation of the pattern through etching, the resist underlayer film can be easily removed while minimizing the influence exerted on the substrate.

Hereinafter, each step will be explained.

Resist Underlayer Film-Providing Step

In this step, a resist underlayer film is provided directly or indirectly on a substrate using the composition for forming a resist underlayer film.

The substrate is exemplified by a silicon wafer, a wafer covered with aluminum, and the like.

As described above, in the pattern-forming method, the stepped substrates, the substrates having a plurality of types of trenches and the like can be also suitably used, and a resist underlayer film superior in flatness can be formed.

As a substrate having a plurality of types of trenches, a substrate having trenches differing from one another in terms of an aspect ratio can be also suitably used, for example. A substrate that involves various values of the aspect ratio may also be used; for example, the ratio of the maximum value to the minimum value of the aspect ratios of the trenches of the substrate is preferably no less than 3, more preferably no less than 5, still more preferably no less than 10, and particularly preferably no less than 15.

The procedure for applying the composition for forming a resist underlayer film to the substrate is not particularly limited, and applying the composition may be carried out by an appropriate procedure such as, for example, spin-coating, cast coating and roll coating.

Moreover, after applying the composition for forming a resist underlayer film, heating is typically executed for the purpose of removing the solvent from the coating film.

The film thickness of the resist underlayer film provided is preferably 10 nm to 5 μm, and more preferably 30 nm to 0.5 μm.

Intermediate Layer-Providing Step

In this step, an interlayer is provided directly or indirectly on the resist underlayer film provided in the resist underlayer film-providing step. The intermediate layer has functions exhibited by the resist underlayer film and/or the resist film in the resist pattern formation for the purpose of reinforcing the abovementioned functions, or has functions not exhibited by the resist underlayer film and/or the resist film in the resist pattern formation for the purpose of imparting the unexhibited functions. For example, in a case where an antireflective film is provided as the intermediate layer, a reflection-preventive function of the resist underlayer film can be reinforced.

The intermediate layer may be provided using an organic compound or an inorganic oxide. Examples of the organic compound include materials commercially available from Brewer Science, Inc. under the trade name "DUV-42", "DUV-44", "ARC-28", "ARC-29" and the like, and materials commercially available from Rohm & Haas Company under the trade name "AR-3", "AR-19" and the like, etc. Moreover, examples of the inorganic oxide include materials commercially available from JSR Corporation under the trade name "NFC SOG" series, and polysiloxanes, titanium oxide, oxidized alumina, tungsten oxide, or the like which are formed by a CVD process may be used.

The procedure for providing the intermediate layer is exemplified by, but not particularly limited to, a coating procedure, a CVD process, and the like. Of these, the coating procedure is preferred. In a case where the coating procedure is employed, the intermediate layer can be provided consecutively after providing the resist underlayer film.

Moreover, although the film thickness of the intermediate layer is not particularly limited and appropriately selected in accordance with the functions required for the intermediate layer, the film thickness of the intermediate layer is preferably 10 nm to 3 μm, and more preferably 20 nm to 0.3 μm.

Resist Pattern-Forming Step

In this step, a resist pattern is formed directly or indirectly on the resist underlayer film. This step is exemplified by a procedure involving photolithography, and the like. Hereinafter, this procedure will be specifically explained.

An exemplary procedure involving photolithography includes:

providing a resist film directly or indirectly on the resist underlayer film using a resist composition (hereinafter, may be also referred to as "resist film-providing step");

exposing the resist film (hereinafter, may be also referred to as "exposure step"); and developing the resist film exposed (hereinafter, may be also referred to as "development step").

Resist Film-Providing Step

In this step, a resist film is provided directly or indirectly on the resist underlayer film using a resist composition. Specifically, after the resist composition is applied such that the resulting resist film has a predetermined film thickness, pre-baking is executed to evaporate the solvent in the coating film, whereby the resist film is provided.

The resist composition is exemplified by: a positive type or negative type chemical amplification resist composition that contains a photoacid generating agent; a positive type resist composition that contains an alkali-soluble resin and a quinone diazide photosensitizing agent; a negative type resist composition that contains an alkali-soluble resin and a crosslinking agent; and the like.

The solid content concentration of the resist composition is preferably 5 to 50% by mass. In addition, the resist composition is preferably prepared after filtration thereof through a filter having a pore size of about 0.2 p.m. It is to be noted that in this step, a commercially available resist composition may be directly used.

The procedure for applying the resist composition is not particularly limited, and applying the resist composition may be carried out by an appropriate procedure such as, for example, spin-coating, cast coating, roll coating.

Moreover, the prebaking temperature may be appropriately selected in accordance with the type of the resist composition used and the like, but is preferably 30° C. to 200° C., and more preferably 50° C. to 150° C.

Exposure Step

In this step, the resist film provided in the resist film-providing step is exposed. The exposure is executed through a certain mask pattern, and a liquid immersion liquid, as needed.

The exposure light may be appropriately selected in accordance with the type of the photoacid generating agent used in the resist composition, from e.g., electromagnetic waves such as visible light rays, ultraviolet rays, far ultraviolet rays, X-rays and γ-rays; particle rays such as electron beams, molecular beams, ion beams and α-rays; and the like. However, the far ultraviolet rays are preferred; a KrF excimer laser beam (248 nm), an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm), an extreme ultraviolet ray (wavelength: 13 nm, etc.) are more preferred; and an ArF excimer laser beam is still more preferred.

In order to improve the resolution, the pattern profile, the developability, etc. of the formed resist pattern, post-baking may be executed after the exposure. The temperature of the post-baking may be appropriately adjusted in accordance with the type of the resist composition used and the like, but is preferably 50° C. to 200° C., and more preferably 70° C. to 150° C.

Development Step

In this step, the resist film exposed in the exposure step is developed.

The developer solution which may be used in the development may be appropriately selected in accordance with the type of the resist composition used. For a development with an alkali, specific examples of the developer solution includes: aqueous alkaline solutions such as sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene and 1,5-diazabicyclo[4.3.0]-5-nonene; and the like. It is to be noted that in a case where the interlayer-providing step is executed to provide the intermediate layer, the influence of these aqueous alkaline solutions on the resist underlayer film can be minimized.

An appropriate amount of water soluble organic solvent, for example, an alcohol such as methanol and ethanol, and/or a surfactant may be added to these aqueous alkaline solutions.

Moreover, an organic solvent-containing developer solution may be used as the developer solution. Examples of the organic solvent include esters, ketones, ethers, alcohols, amides, hydrocarbons, and the like. The development with an organic solvent has a minor influence on the resist underlayer film.

After the development with the developer solution, washing and drying are executed, whereby a predetermined resist pattern is formed.

Moreover, a procedure involving nanoimprinting, a procedure involving the use of a directed self-assembling composition, and the like may be also used as the procedure for executing the resist pattern-forming step in place of the procedure involving photolithography described above.

Substrate Pattern-Forming Step

In this step, a pattern is formed on the substrate through dry etching of the resist underlayer film, the substrate, or both the resist underlayer film and the substrate using the resist pattern as a mask. It is to be noted that in a case where the intermediate layer is provided, the intermediate layer is further dry etched.

The dry etching may be executed using a well-known dry etching apparatus. In addition, depending on the elemental composition of a substance to be etched, the following gases may be used as a sauce gas in the dry etching: oxygen atom-containing gases such as $O_2$, CO and $CO_2$; inert gases such as He, $N_2$ and Ar; chlorine-based gases such as $Cl_2$ and $BCl_3$; fluorine-based gases such as $CHF_3$ and $CF_4$; and other gas such as $H_2$ and $NH_3$. It is to be noted that these gases may also be used in mixture.

Step of Subjecting Resist Underlayer Film to Heating or Acid Treatment

The pattern-forming method according to the embodiment of the present invention further includes subjecting the resist underlayer film to heating or an acid treatment before the removing step described later. According to this step, a part or all of organic groups substituting the hydrogen atom of phenolic hydroxyl groups included in the compound (A) constituting the resist underlayer film are dissociated to generate a phenolic hydroxyl group. Due to the phenolic hydroxyl group being thus generated in the compound (A), the resist underlayer film can be easily removed with a basic solution.

The procedure for allowing a part or all of the organic groups to be dissociated is preferably heating of the resist underlayer film. The temperature of the heating is preferably 100° C. to 330° C., more preferably 200° C. to 320° C., and still more preferably 240° C. to 300° C. In addition, the time period for the heating is preferably 10 sec to 600 sec, and more preferably 30 sec to 240 sec. Furthermore, the oxygen concentration in the heating is preferably no less than 5% by volume, and still more preferably no less than 20% by volume.

It is to be noted that in a case where the composition for forming a resist underlayer film contains a thermal acid generating agent or the like, dissociation of the organic group is catalyzed by an acid generated from the thermal acid generating agent or the like upon the heating. Consequently, the dissociation of the organic group can be achieved at lower temperatures.

In addition to the procedure involving heating, the procedure for allowing the organic group to be dissociated is also exemplified by a procedure involving treating the resist underlayer film with an acid. The procedure for treating the resist underlayer film with an acid is exemplified by: a procedure involving washing with an acid; a procedure involving irradiating the resist underlayer film with light in a case where the composition for forming a resist underlayer film contains a photoacid generating agent or the like; and the like.

The time point when the step of subjecting the resist underlayer film to heating or an acid treatment is executed is not particularly limited as long as this step is executed before the removing step in the pattern-forming method. For example, this step may be executed at any time point described in the following, or a combination of two or more thereof: after the resist underlayer film-providing step and before the resist pattern-forming step (i.e., before the resist underlayer film-providing step and after the intermediate layer-providing step, or after the intermediate layer-providing step and before the resist pattern-forming step); after the resist pattern-forming step and before the substrate pattern-forming step; after the substrate pattern-forming step; or concurrently with the resist underlayer film-providing step, the resist pattern-forming step or the substrate pattern-forming step. Of these, in light of ease of operation, this step is executed preferably: concurrently with the resist underlayer film-providing step, in other words, in the heating for providing a resist underlayer film or the like; or after the substrate pattern-forming step, in other words, using the resist underlayer film obtained after the etching step.

Removing Step

In the removing step, the resist underlayer film on the substrate is removed with a basic solution.

Although the basic solution used in this step is not particularly limited as long as the solution is basic, examples thereof include basic aqueous solutions of sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide (TMAH), tetraethylammonium hydroxide, pyrrole, piperidine, choline, 1,8-diazabicyclo[5.4.0]-7-undecene, 1,5-diazabicyclo[4.3.0]-5-nonene, or the like. Of these, an aqueous TMAH solution is preferred. Alternatively, an appropriate amount of a water soluble organic solvent, for example, an alcohol such as methanol and ethanol, and/or a surfactant may be added to these basic aqueous solutions. Moreover, solutions containing an organic solvent in addition to or instead of water may be used as long as the solutions are basic.

The pH of the basic solution is, for example, preferably no less than 7.5, and still more preferably no less than 8. When the pH is less than 7.5, the resist underlayer film is less likely to be sufficiently removed.

The procedure for removing the resist underlayer film with the basic solution is not particularly limited as long as the resist underlayer film is brought into contact with the basic solution for a certain time period; examples thereof include: a procedure that involves immersing the patterned substrate in the basic solution; a procedure that involves spraying the basic solution; a procedure that involves coating the basic solution; and the like. It is to be noted that the time period for the immersion in the procedure that involves immersing is, for example, 0.2 min to 30 min. After the completion of any of these procedures, the substrate is preferably washed with water, and dried.

According to the pattern-forming method, the resist underlayer film is removed with the basic solution after forming a pattern on a substrate by etching, as described above. Accordingly, the resist underlayer film can be easily removed while minimizing the influence exerted on the substrate. In particular, according to the pattern-forming method, even when a low dielectric material which is likely to be affected by ashing or the like is used as the substrate, the resist underlayer film can be removed while minimizing the influence on the substrate.

EXAMPLES

Hereinafter, the present invention is explained in detail by way of Examples, but the present invention is not in any way limited to these Examples. Measuring methods for various types of physical properties are shown below.
Confirmation of Structure of Compound (A)

The structure of the compound (A) was confirmed based on the molecular weight as determined by means of MALDI-TOF-MS (SHIMAZU/KRATOS matrix-assisted laser desorption/ionization time-of-flight mass spectrometry apparatus KOMPACT MALDI IV tDE, manufactured by Shimadzu Corporation), an infrared absorption spectrum (IR) recorded on a Fourier transform infrared spectrometer (FT-IR) (model 420, manufactured by JASCO Corporation), and a $^1$H-NMR spectrum recorded on a nuclear magnetic resonance apparatus (model JNM-ECA-500, manufactured by JEOL, Ltd.) with a solvent for measurement of DMSO-$d_6$.
Mw of Resin (C)

The Mw of the resin (C) was determined by gel permeation chromatography using GPC columns (G2000HXL×2 and G3000HXL×1, manufactured by Tosoh Corporation), a "differential refractometer" as a detector, and mono-dispersed polystyrene as a standard under an analytical condition involving a flow rate of 1.0 mL/min, an elution solvent of tetrahydrofuran, and a column temperature of 40° C.

Synthesis of Compound (A)

Synthesis Example 1

Synthesis of Compound (A-1)

(1-1)
Into a 1,000 mL three-neck eggplant shaped flask were charged 35 g of resorcinol, 39 g of p-hydroxybenzaldehyde and 450 g of ethanol, and dissolution was completed at room temperature under a nitrogen atmosphere. To the resulting solution was added dropwise 95.6 g of concentrated hydrochloric acid over 1 hour at the solution temperature of 40° C., then the solution temperature was elevated to 80° C., and the mixture was aged for 11 hrs. After the aging, the flask was cooled until the solution temperature dropped to room temperature. Thereafter, filtration was carried out in order to remove the ethanol solution, whereby a reddish brown solid matter deposited was recovered. The reddish brown solid matter was washed with a flowing mixed solution of methanol/water (each 300 g), and then dried under reduced pressure at 60° C. overnight to obtain 43.6 g of a precursor X having phenolic hydroxyl groups as a pink solid matter. It was confirmed by $^1$H-NMR that the intended precursor X was obtained.

(1-2)
Next, in a 500 mL round-bottom flask, 10.0 g of the precursor X obtained in (1-1) described above was dissolved in 200 mL of N,N-dimethylacetamide under a nitrogen atmosphere with stirring by means of a magnetic stirrer. Under the stirring, 21.4 g of 2-chloromethylstyrene was added to the resulting solution, then 28.4 g of potassium carbonate was further added thereto, and the reaction was allowed to proceed at 80° C. for 18 hrs. After completing the reaction, the reaction solution was added to 2 L of water to which 14 mL of acetic acid was added. The supernatant liquid was removed. The residual highly viscous matter was dissolved in a minimum amount of acetone, and the solution was charged into 500 mL of water to permit reprecipitation. The resulting highly viscous matter was dried under reduced pressure at 65° C. overnight to obtain 12.5 g of a compound (A-1) as a brown solid.

Synthesis Examples 2 to 24

Synthesis of Compounds (A-2) to (A-24)

Compounds (A-2) to (A-24) (compounds represented by the following formulae (A-2) to (A-24)) were synthesized in a similar manner to Synthesis Example 1 except that the phenolic compound, the aldehyde compound, and the compound used for substitution of the hydrogen atom included in the phenolic hydroxyl group were appropriately changed.

Synthesis Example 25

Synthesis of Compound (A-25)

Into a reaction apparatus equipped with a condenser, a thermometer and a stirrer were charged 100 parts by mass of resorcinol and 200 parts by mass of ethanol, and 68 parts by mass of hydrochloric acid was further added thereto. This solution was cooled to 5° C. with stirring, 45 parts by mass of 50% by mass aqueous 1,5-pentanedial solution was slowly added dropwise. Thereafter, the mixture was heated at 80° C. for 48 hrs, whereby a yellow turbid suspension was obtained. After the suspension was poured into methanol, precipitates were recovered by filtration, and washed three times with methanol. The obtained precipitates were dried under reduced pressure at room temperature for 24 hrs, whereby a light yellow solid was obtained as a powder. Next, to 100 parts by mass of the obtained light yellow solid were added 23 parts by mass of tetrabutylammonium bromide and 350 parts by mass of anhydrous pyridine, and the mixture was stirred for 1 hour. Thereafter, 185 parts by mass of di-t-butyl dicarbonate was slowly added, and the mixture was stirred at room temperature for 48 hrs. After completing the reaction, the reaction liquid was poured into 300 mL of a 3% by mass aqueous oxalic acid solution to permit deposition of a solid. Thereafter, the resulting solid was dissolved in methylene chloride, then washed three times with 100 mL of a 3% by mass aqueous oxalic acid solution, and thereafter washed with 100 mL of water. After removing the water layer, the organic layer was dried over anhydrous magnesium sulfate. Thereafter, purification by silica gel column chromatography using hexane:ethyl acetate (1:1 (volume ratio)) as an eluent was carried out to obtain a compound (A-25) (a compound represented by the following formula (A-25)).

With respect to the compounds (A-1) to (A-25) obtained in Synthesis Examples 1 to 25 described above, Rs in the following formulae represent a hydrogen atom or a group represented by the corresponding formula; and * denotes a binding site with respect to the oxygen atom. In addition, $^1$H-NMR analysis of each compound (A) was carried out, and consequently it was found that a ratio of the number of substituted phenolic hydroxyl groups to the number of unsubstituted phenolic hydroxyl groups (substituted phenolic hydroxyl group/unsubstituted phenolic hydroxyl group) (hereinafter, may be also referred to as "number ratio "a"") was as shown in Table 1 below. More specifically, in a case where the number ratio "a" is x/y, wherein a sum of x and y is equal to 100, x (%) of Rs included in each compound (A) represent the group represented by the following formula as R, whereas y (%) of Rs represent a hydrogen atom.

(A-1)

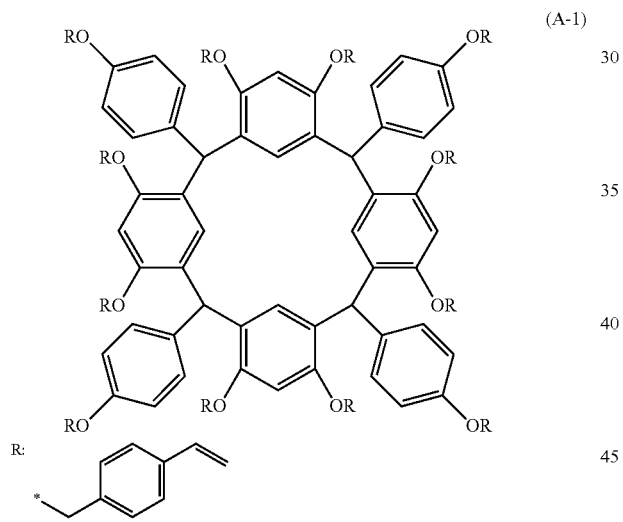

R:

(A-2)

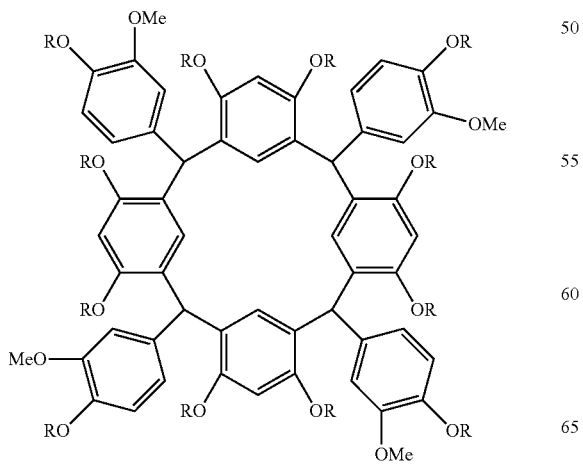

(A-3)

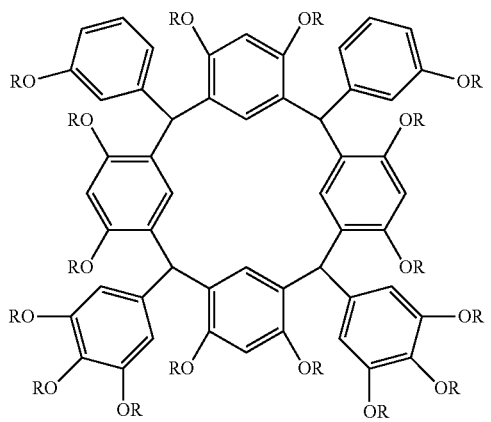

R:

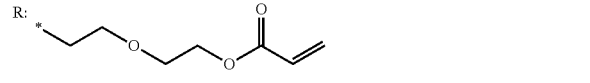

(A-4)

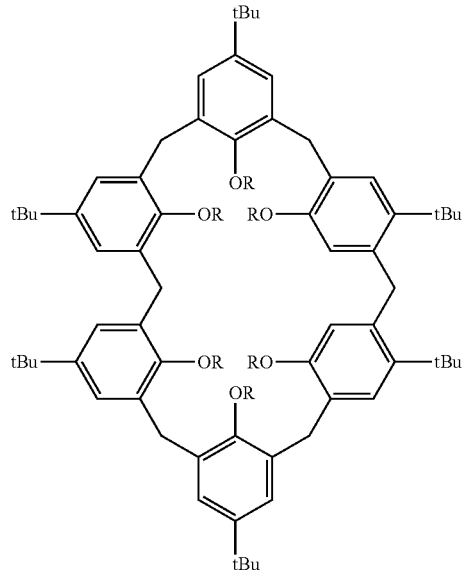

(A-5)

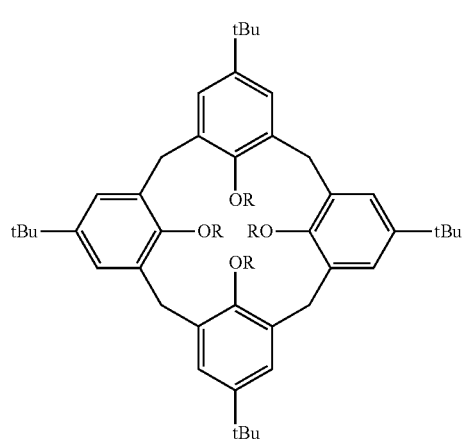

27
-continued
R: 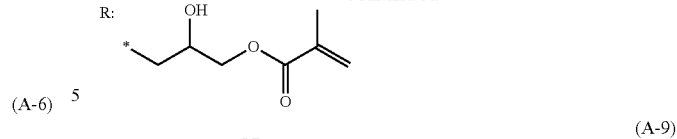
(A-6)
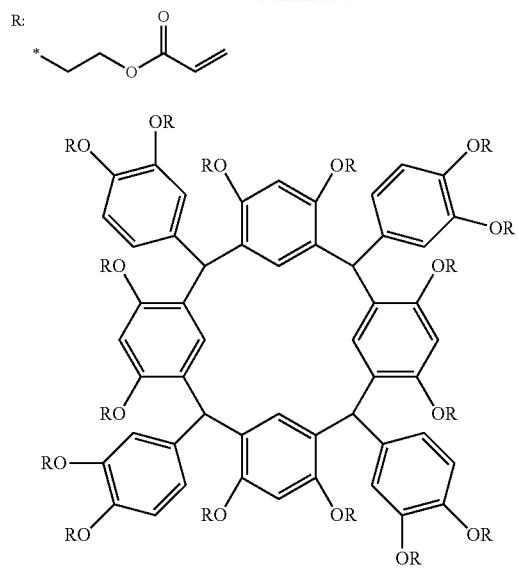
(A-9)
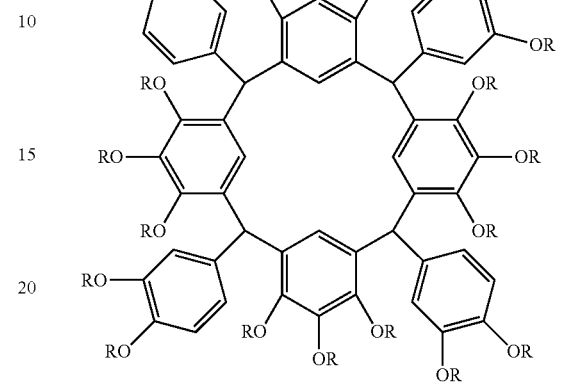
(A-7)
28
-continued
(A-10)
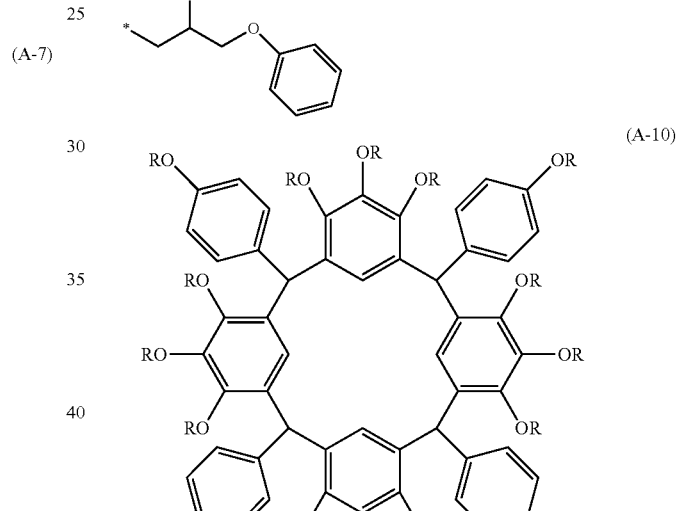
(A-8)
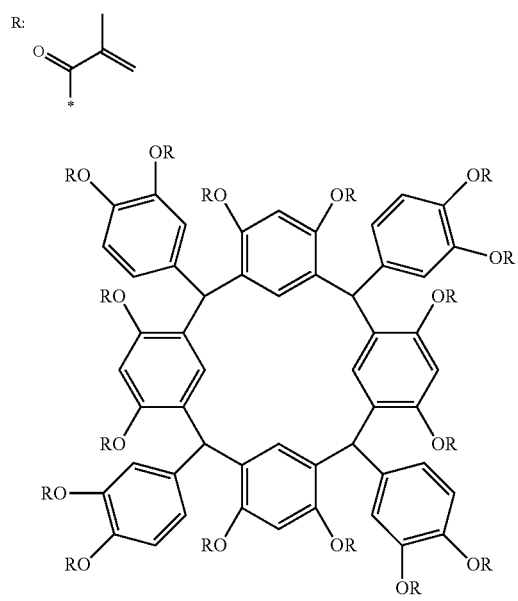
(A-11)
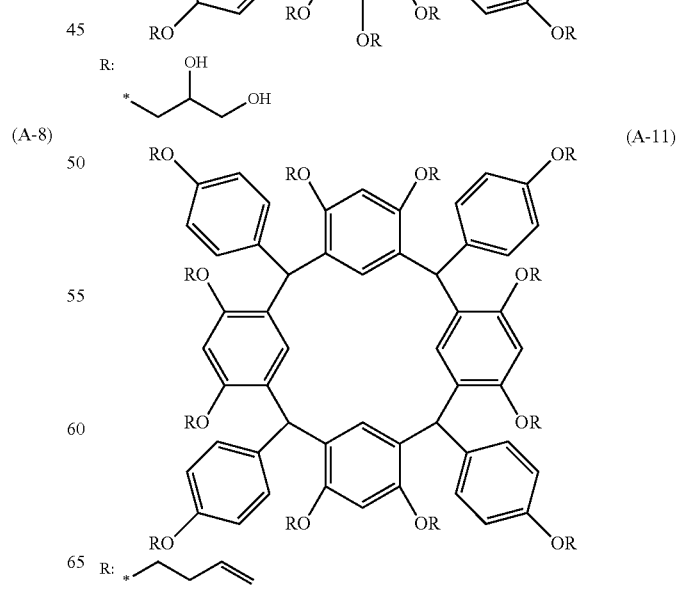

-continued
(A-12)
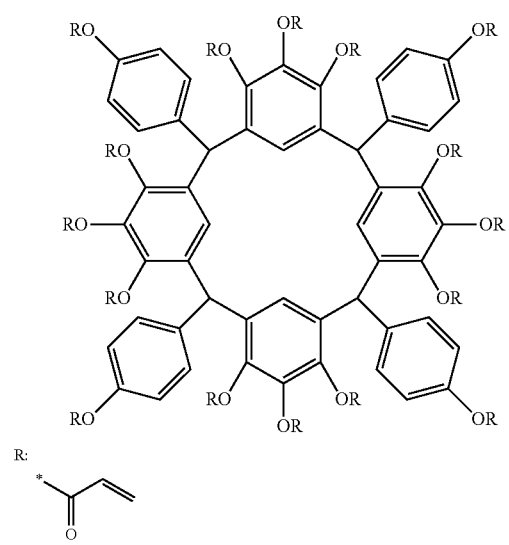
(A-13)
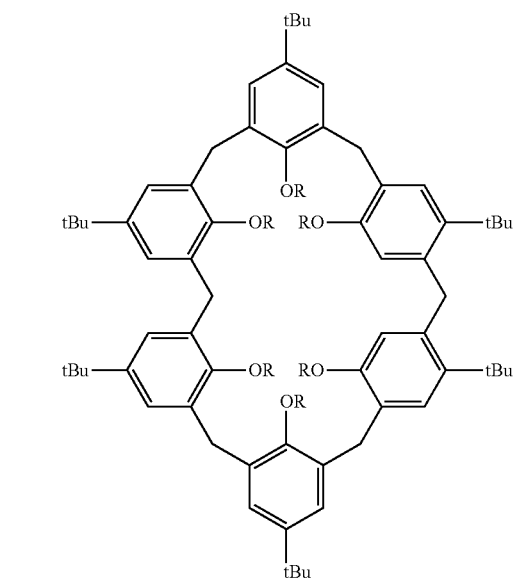
(A-14)
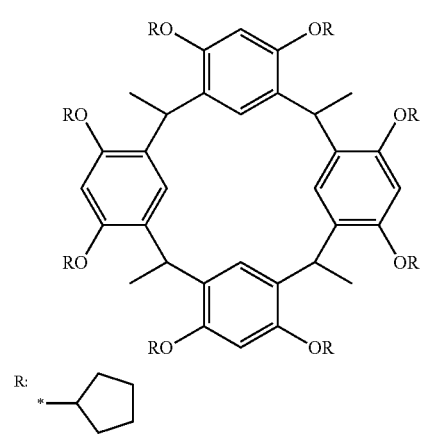
-continued
(A-15)
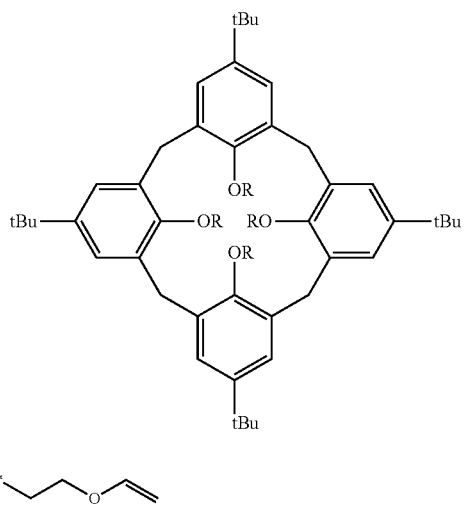
(A-16)
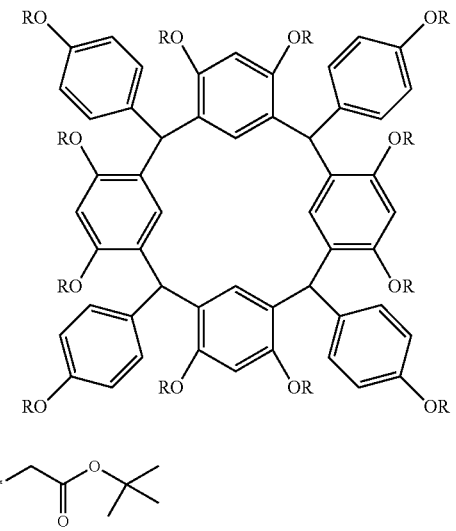
(A-17)
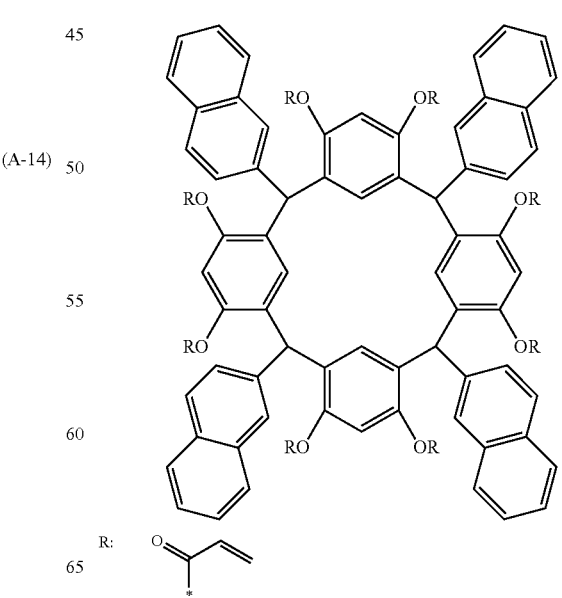

(A-18)
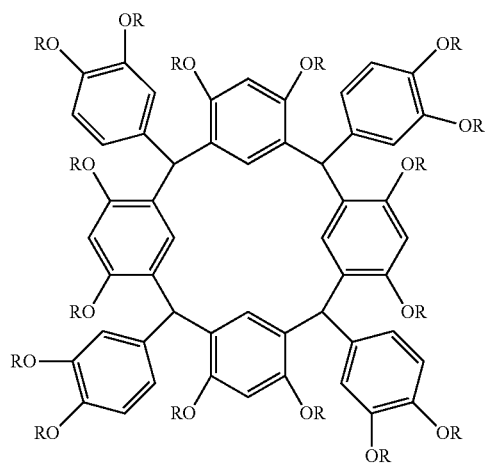
R: 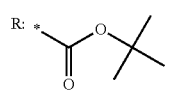
(A-19)
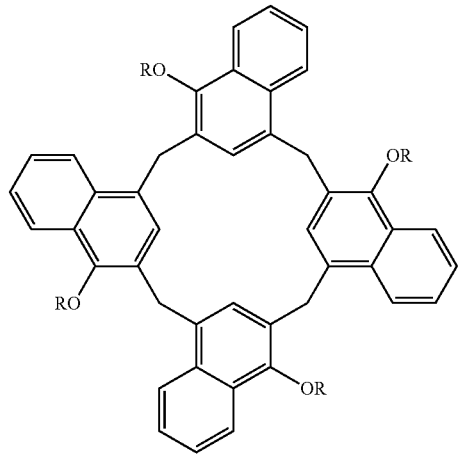
R: 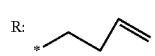
(A-20)
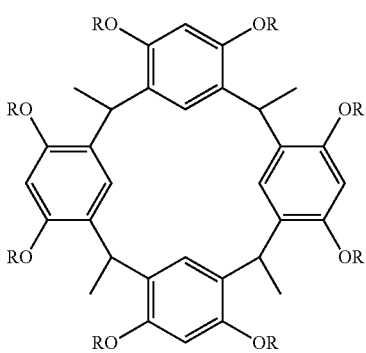
R: 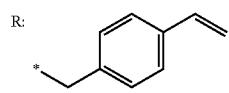
(A-21)
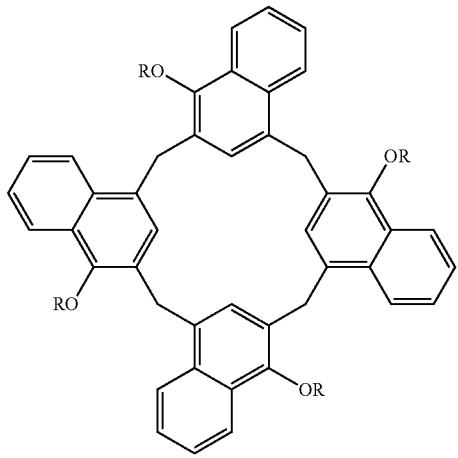
R: 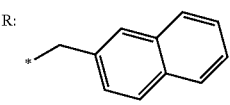
(A-22)
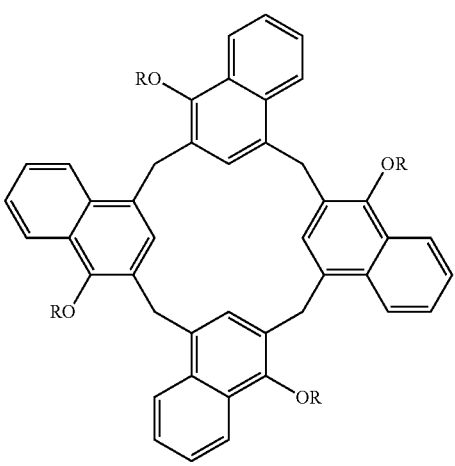
R: 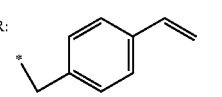
(A-23)
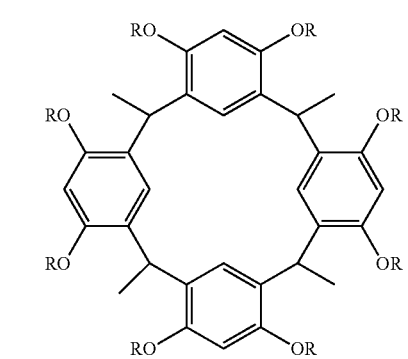
R: 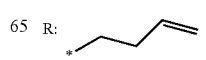

-continued

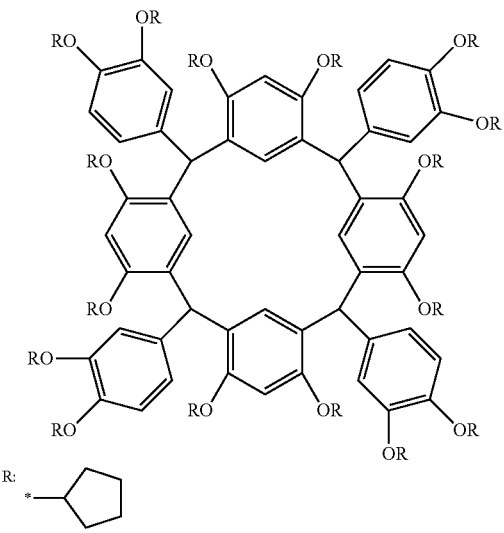

(A-24)

R: *—[cyclopentyl]

(A-25)

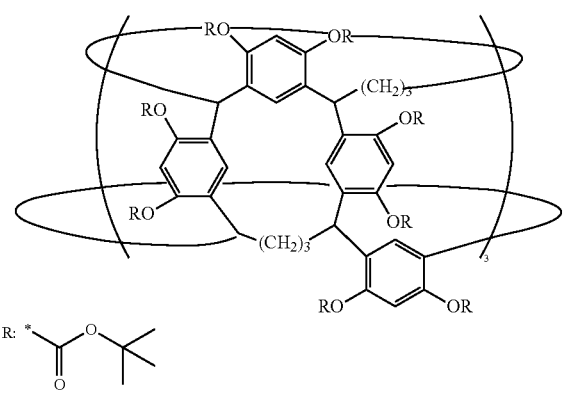

R: *—O—C(=O)—O—C(CH3)3

TABLE 1

| (A) Compound | Number ratio "a" (number of substituted phenolic hydroxyl groups/ number of unsubstituted phenolic hydroxyl groups) |
|---|---|
| A-1 | 70/30 |
| A-2 | 80/20 |
| A-3 | 90/10 |
| A-4 | 80/20 |
| A-5 | 70/30 |
| A-6 | 80/20 |
| A-7 | 80/20 |
| A-8 | 80/20 |
| A-9 | 70/30 |
| A-10 | 80/20 |
| A-11 | 80/20 |
| A-12 | 80/20 |
| A-13 | 70/30 |
| A-14 | 80/20 |
| A-15 | 70/30 |
| A-16 | 80/20 |
| A-17 | 75/25 |
| A-18 | 80/20 |
| A-19 | 80/20 |
| A-20 | 75/25 |
| A-21 | 70/30 |
| A-22 | 80/20 |
| A-23 | 80/20 |
| A-24 | 80/20 |
| A-25 | 50/50 |

The calixarene (compound (a-1)) used in the composition for forming a resist underlayer film according to Comparative Example is shown below.

(a-1)

Synthesis of Resin (C)

Synthesis Example 26

Synthesis of Resin (C-1)

Into a separable flask equipped with a thermometer were charged 10 parts by mass of 2,7-naphthalenediol/formaldehyde condensate (a resin including hydroxy groups), 10 parts by mass of propargyl bromide, 10 parts by mass of triethylamine and 40 parts by mass of tetrahydrofuran, and the reaction was allowed to proceed at 50° C. for 12 hrs with stirring. After completing the reaction, the reaction solution was cooled to 30° C. or below by water-cooling. After the cooling, the reaction solution was charged into a large amount of n-heptane. Thereafter, the deposited solid was separated by decantation, and washed with a large amount of n-heptane. Subsequently, the solid was dissolved in methyl isobutyl ketone, and washed sequentially with a 1% by mass aqueous oxalic acid solution and pure water to eliminate residual triethylamine. Then, the resulting organic layer was concentrated, and dried at 50° C. for 17 hrs, whereby a resin (C-1) was obtained. The resin (C-1) had an Mw of 4,500, and the percentage of the propargyl group introduced into the resin (C-1) was 90% with respect to the total hydroxy groups.

Preparation of Composition for Forming Resist Underlayer Film

Each component used in the preparation of compositions for forming a resist underlayer film is shown below.

(B) Organic Solvent
 B-1: propylene glycol monomethyl ether acetate
 B-2: propylene glycol monomethyl ether
(D) Acid Generating Agent
 D-1: bis(4-t-butylphenyl)iodonium nonafluoro-n-butanesulfonate (a compound represented by the following formula (D-1))

(D-1)

(E) Crosslinking Agent

E-1: 1,3,4,6-tetrakis(methoxymethyl)glycoluril (a compound represented by the following formula (E-1))

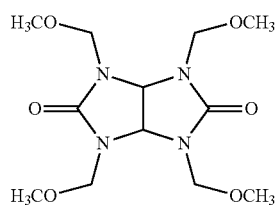

(E-1)

Example 1

Preparation of Composition for Forming Resist Underlayer Film (U-1)

A solution was prepared by dissolving 5 parts by mass of the resin (A-1) obtained in Synthesis Example 1 in 95 parts by mass of propylene glycol monomethyl acetate (organic solvent (B-1)). Thereafter, this solution was filtered through a membrane filter having a pore size of 0.1 μm to prepare a composition for forming a resist underlayer film (U-1).

Examples 2 to 28 and Comparative Example 1

Preparation of Compositions for Forming Resist Underlayer Film (U-2) to (U-28) and (CU-1)

Compositions for forming a resist underlayer film (U-2) to (U-28) and (CU-1) were prepared in a similar manner to Example 1 except that the type and the content of the components used were as shown in Tables 2-1 and 2-2 below. It is to be noted that "-" in Tables 2-1 and 2-2 indicates that the corresponding component was not used.

TABLE 2-1

| | Composition for forming resist underlayer film | (A) Component type | content (parts by mass) | (B) Organic solvent type | content (parts by mass) | (C) Resin type | content (parts by mass) | (D) Acid generating agent type | content (parts by mass) | (E) Crosslinking agent type | content (parts by mass) |
|---|---|---|---|---|---|---|---|---|---|---|---|
| Example 1 | U-1 | A-1 | 5 | B-1 | 95 | — | — | — | — | — | — |
| Example 2 | U-2 | A-3 | 5 | B-1 | 95 | — | — | — | — | — | — |
| Example 3 | U-3 | A-6 | 2.5 | B-1 | 95 | C-1 | 2.5 | — | — | — | — |
| Example 4 | U-4 | A-7 | 5 | B-1 | 95 | — | — | — | — | — | — |
| Example 5 | U-5 | A-8 | 5 | B-1 | 95 | — | — | — | — | — | — |
| Example 6 | U-6 | A-11 | 5 | B-1 | 95 | — | — | — | — | — | — |
| Example 7 | U-7 | A-12 | 5 | B-1 | 95 | — | — | — | — | — | — |
| Example 8 | U-8 | A-13 | 5 | B-1 | 95 | — | — | — | — | — | — |
| Example 9 | U-9 | A-15 | 5 | B-1 | 95 | — | — | — | — | — | — |
| Example 10 | U-10 | A-17 | 5 | B-1 | 95 | — | — | — | — | — | — |
| Example 11 | U-11 | A-20 | 2.5 | B-1 | 95 | C-1 | 2.5 | — | — | — | — |
| Example 12 | U-12 | A-2 | 2.5 | B-1 | 95 | C-1 | 2.5 | — | — | — | — |
| Example 13 | U-13 | A-4 | 2.5 | B-1 | 95 | C-1 | 2.5 | — | — | — | — |
| Example 14 | U-14 | A-5 | 5 | B-1 | 95 | — | — | D-1 | 5 | E-1 | 10 |
| Example 15 | U-15 | A-9 | 2.5 | B-1 | 95 | C-1 | 2.5 | — | — | — | — |
| Example 16 | U-16 | A-10 | 5 | B-1 | 95 | — | — | D-1 | 5 | E-1 | 10 |
| Example 17 | U-17 | A-14 | 2.5 | B-1 | 95 | C-1 | 2.5 | — | — | — | — |
| Example 18 | U-18 | A-24 | 2.5 | B-1 | 95 | C-1 | 2.5 | — | — | — | — |
| Example 19 | U-19 | A-1/A-16 | 2.5/2.5 | B-1 | 95 | — | — | — | — | — | — |
| Example 20 | U-20 | A-17/A-18 | 2.5/2.5 | B-1 | 95 | — | — | — | — | — | — |

TABLE 2-2

| | Composition for forming resist underlayer film | (A) Component type | content (parts by mass) | (B) Organic solvent type | content (parts by mass) | (C) Resin type | content (parts by mass) | (D) Acid generating agent type | content (parts by mass) | (E) Crosslinking agent type | content (parts by mass) |
|---|---|---|---|---|---|---|---|---|---|---|---|
| Example 21 | U-21 | A-14/A-20 | 1.25/1.25 | B-1 | 95 | C-1 | 2.5 | — | — | — | — |
| Example 22 | U-22 | A-22 | 2.5 | B-1 | 95 | C-1 | 2.5 | — | — | — | — |
| Example 23 | U-23 | A-21 | 2.5 | B-1 | 95 | C-1 | 2.5 | — | — | — | — |
| Example 24 | U-24 | A-23 | 5 | B-1 | 95 | — | — | — | — | — | — |
| Example 25 | U-25 | A-19 | 2.5 | B-1 | 95 | C-1 | 2.5 | — | — | — | — |
| Example 26 | U-26 | A-25 | 5 | B-1 | 95 | — | — | — | — | — | — |
| Example 27 | U-27 | A-14 | 5 | B-1 | 95 | — | — | — | — | — | — |

TABLE 2-2-continued

| Composition for forming resist underlayer film | (A) Component type | (A) Component content (parts by mass) | (B) Organic solvent type | (B) Organic solvent content (parts by mass) | (C) Resin type | (C) Resin content (parts by mass) | (D) Acid generating agent type | (D) Acid generating agent content (parts by mass) | (E) Crosslinking agent type | (E) Crosslinking agent content (parts by mass) |
|---|---|---|---|---|---|---|---|---|---|---|
| Example 28 | U-28 | A-24 | 5 | B-1 | 95 | — | — | — | — | — | — |
| Comparative Example 1 | CU-1 | a-1 | 5 | B-2 | 95 | — | — | — | — | — | — |

Formation of Resist Underlayer Film

Examples 1 to 28 and Comparative Example 1

Each composition for forming a resist underlayer film prepared in Examples and Comparative Example described above was applied on a silicon wafer (substrate) by way of a spin coating procedure. Thereafter, baking was carried out at 250° C. for 60 sec under an ambient air atmosphere (however, in Example 25, baking was carried out at 250° C. for 60 sec, and further at 350° C. for 60 sec) to form a resist underlayer film having a film thickness of 200 nm, whereby each "resist underlayer film-carrying substrate" in which the resist underlayer film is formed on the substrate was obtained.

Evaluations

The compositions for forming a resist underlayer film obtained above or the resist underlayer film-carrying substrates obtained therefrom were evaluated for the following items in accordance with the following methods. The results of the evaluations are shown in Tables 3-1 and 3-2.

Solubility in PGMEA

Each composition for forming a resist underlayer film obtained above was added to a PGMEA (propylene glycol monomethyl ether acetate) solvent to execute a solubility test. The solubility in PGMEA was evaluated to be "A" (favorable) in a case where the composition for forming a resist underlayer film was dissolved in the solution without any turbidness and/or deposited matter, and to be "B" (unfavorable) in a case where turbidness and/or deposited matter were/was found in the solution.

Etching Resistance

The resist underlayer film of the resist underlayer film-carrying substrate obtained above was etched using an etching apparatus (trade name "EXAM", manufactured by Shinko Seiki Co., Ltd.), with $CF_4/Ar/O_2$ ($CF_4$: 40 mL/min, Ar: 20 mL/min, $O_2$: 5 mL/min; pressure: 20 Pa; RF power: 200 W; treatment time period: 40 sec; and temperature: 15° C.). Then, the film thickness of the resist underlayer film was measured before and after the etching treatment, followed by calculation of an etching rate, and the etching resistance was evaluated based on the etching rate. It is to be noted that the calculation of the etching rate was carried out by using as a reference resist underlayer film, a resist underlayer film formed from a composition for forming a resist underlayer film (trade name "NFC CTL53", manufactured by JSR Corporation). The etching resistance was evaluated to be "S" (superior) in a case where an improvement by greater than 10% was found as compared with the reference resist underlayer film (i.e., the etching rate being less than 90%), to be "A" (favorable) in a case where the etching rate was no less than 90% and less than 110%, and to be "B" (somewhat favorable) in a case where the etching rate was no less than 110%.

Solvent Resistance

Each resist underlayer film-carrying substrate obtained above was immersed in cyclohexanone at room temperature for 1 min. The film thickness was measured before and after the immersion using a spectroscopic ellipsometer (UV 1280E, manufactured by KLA-TENCOR), and a rate of change of the film thickness was calculated based on the measured values. The solvent resistance was evaluated to be "A" (favorable) in a case where the rate of change of the film thickness was less than 1%, to be "B" (somewhat favorable) in a case where the rate of change of the film thickness was no less than 1% and less than 5%, and to be "C" (unfavorable) in a case where the rate of change of the film thickness was no less than 5%.

Flatness

Each of the compositions for forming a resist underlayer film of Examples and Comparative Examples described above was applied on a $SiO_2$ stepped substrate on which trenches having a width of 42 nm, a pitch of 84 nm and a depth of 180 nm (aspect ratio: 4.3), trenches having a width of 100 nm, a pitch of 150 nm and a depth of 180 nm (aspect ratio: 1.8), and trenches having a width of 5 μm and a depth of 180 nm (open spaces; aspect ratio: 0.036) were provided in combination (the ratio of the maximum value to the minimum value of the aspect ratios in the plurality of types of trenches: 119). Thereafter, baking was carried out at 250° C. for 60 sec under an ambient air atmosphere to form a resist underlayer film having a film thickness of 200 nm. The shape of the resist underlayer film was observed using a scanning electron microscope (S-4800, manufactured by Hitachi High-Technologies Corporation), and the difference of the maximum value and the minimum value of the film thicknesses of the resist underlayer film on the Trench or spaces (ΔFT) was determined. The flatness was evaluated to be "S" (superior) in a case where the ΔFT was less than 10 nm, to be "A" (favorable) in a case where was no less than 10 nm and less than 20 nm, to be "B" (somewhat favorable) in a case where the ΔFT was no less than 20 nm and less than 35 nm; and to be "C" (unfavorable) in a case where the ΔFT was no less than 35 nm.

Outgas Inhibitory Ability

Each of the resist underlayer film-carrying substrate obtained above was cut into a rectangle of 1 cm×5 cm to prepare a sample for measurement. The amount of sublimates in heating of the sample for measurement at 250° C. for 7 min using an automated P & T apparatus (JTD-505, manufactured by Japan Analytical Industry Co., Ltd.) was determined using a gas chromatography mass spectrometry apparatus (GC-MS) (6890N, manufactured by Agilent Technologies). It is to be noted that a resist underlayer film formed from a composition for forming a resist underlayer film (trade name "NFC CTL53", manufactured by JSR Corporation) was used as a reference resist underlayer film. The outgas inhibitory ability was evaluated to be "A" (favorable) in a case where the amount of the sublimates of the sample for measurement was smaller as compared with the amount of the sublimates of the reference resist underlayer film, to be "B" (somewhat favorable) in a case where no significant difference was not found between the amount of the sublimates of the sample for measurement and the amount of the sublimates of the reference resist underlayer film, and to be "C" (unfavorable) in a case where the amount of the sublimates of the sample for measurement was greater as compared with the amount of the sublimates of the reference resist underlayer film.

Storage Stability

Each of the compositions for forming a resist underlayer film obtained above was stored at a temperature of 23° C., and after three months had passed, the molecular weight of the compound (A) contained was determined, and the storage stability was evaluated. The storage stability was evaluated to be "A" (favorable) in a case where a change of the molecular weight was not found, and to be "B" (unfavorable) in a case where the change of the molecular weight was found.

underlayer film superior in flatness, solvent resistance and outgas-inhibitory ability to be formed even on a stepped substrate.

The composition for forming a resist underlayer film according to the embodiments of the present invention enables a resist underlayer film superior in flatness, solvent resistance and outgas-inhibitory ability to be formed. The pattern-forming method according to the embodiments of the present invention enables a resist underlayer film superior in flatness, solvent resistance and outgas-inhibitory ability to be formed, and in turn, a favorable pattern to be formed. Therefore, the composition for forming a resist underlayer film and the pattern-forming method can be suitably used for producing semiconductor devices in which further progress of miniaturization is expected in the future.

The following Appendices are embodiments of the present invention.

Appendix 1

A composition for forming a resist underlayer film comprising:

a calixarene-based compound obtained from a calixarene by substituting at least a part of hydrogen atoms each on

TABLE 3-1

| | Composition for forming resist underlayer film | Solubility in PGMEA | Etching resistance | Solvent resistance | Flatness | Outgas inhibitory ability | Storage stability |
|---|---|---|---|---|---|---|---|
| Example 1 | U-1 | A | S | A | S | A | A |
| Example 2 | U-2 | A | A | A | A | A | A |
| Example 3 | U-3 | A | A | A | A | A | A |
| Example 4 | U-4 | A | B | A | A | A | A |
| Example 5 | U-5 | A | B | A | A | A | A |
| Example 6 | U-6 | A | A | A | S | A | A |
| Example 7 | U-7 | A | A | A | A | A | A |
| Example 8 | U-8 | A | S | A | A | A | A |
| Example 9 | U-9 | A | B | A | A | A | A |
| Example 10 | U-10 | A | S | A | A | A | A |
| Example 11 | U-11 | A | S | A | S | A | A |
| Example 12 | U-12 | A | S | A | A | A | A |
| Example 13 | U-13 | A | A | A | S | A | A |
| Example 14 | U-14 | A | B | A | A | A | A |
| Example 15 | U-15 | A | A | A | A | A | A |
| Example 16 | U-16 | A | B | A | A | A | A |
| Example 17 | U-17 | A | A | A | A | A | A |
| Example 18 | U-18 | A | A | A | A | A | A |
| Example 19 | U-19 | A | A | A | A | A | A |
| Example 20 | U-20 | A | A | A | A | A | A |

TABLE 3-2

| | Composition for forming resist underlayer film | Solubility in PGMEA | Etching resistance | Solvent resistance | Flatness | Outgas inhibitory ability | Storage stability |
|---|---|---|---|---|---|---|---|
| Example 21 | U-21 | A | S | A | S | A | A |
| Example 22 | U-22 | A | S | A | S | A | A |
| Example 23 | U-23 | A | S | A | S | A | A |
| Example 24 | U-24 | A | A | A | S | A | A |
| Example 25 | U-25 | A | A | A | S | A | A |
| Example 26 | U-26 | A | B | A | B | B | A |
| Example 27 | U-27 | A | A | B | A | A | A |
| Example 28 | U-28 | A | A | B | A | A | A |
| Comparative Example 1 | CU-1 | B | A | C | C | C | A |

As is seen from the results shown in Tables 3-1 and 3-2, the composition for forming a resist underlayer film according to the embodiment of the present invention enables a resist phenolic hydroxyl groups comprised in the calixarene, with a monovalent organic group having 1 to 30 carbon atoms; and an organic solvent.

Appendix 2

The composition for forming a resist underlayer film according to appendix 1, wherein the monovalent organic group comprises a crosslinkable group.

Appendix 3

The composition for forming a resist underlayer film according to appendix 1, wherein a part of hydrogen atoms each on phenolic hydroxyl groups of the calixarene-based compound is substituted.

Appendix 4

The composition for forming a resist underlayer film according to appendix 3, wherein a ratio of number of substituted phenolic hydroxyl groups to number of unsubstituted phenolic hydroxyl groups in the calixarene-based compound is no less than 30/70 and no greater than 99/1.

Appendix 5

The composition for forming a resist underlayer film according to appendix 1, wherein a viscosity of the composition for forming a resist underlayer film at a solid content concentration of 20% by mass is no less than 1 cps and no greater than 5 cps.

Appendix 6

The composition for forming a resist underlayer film according to appendix 1, wherein the calixarene-based compound is derived from a compound obtained by subjecting a compound represented by a formula (1) and a compound represented by a formula (2) to a condensation reaction,

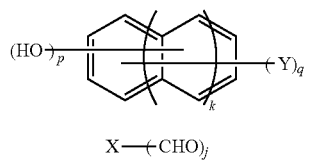

(1)

$$X\text{---}(CHO)_j \quad (2)$$

wherein in the formula (1), Y represents a hydrocarbon group having 1 to 10 carbon atoms; q is an integer of 0 to 7; p is an integer of 1 to 3, wherein a sum of p and q is no less than 1 and no greater than 8; and k is 0 or 1, wherein in a case where q is no less than 2, a plurality of Ys are identical or different, and wherein in the formula (2), X represents a substituted or unsubstituted hydrocarbon group having 1 to 30 carbon atoms and having a valency of j, or hydrogen atom; and j is 1 or 2.

Appendix 7

The composition for forming a resist underlayer film according to appendix 6, wherein the calixarene-based compound is represented by a formula (3),

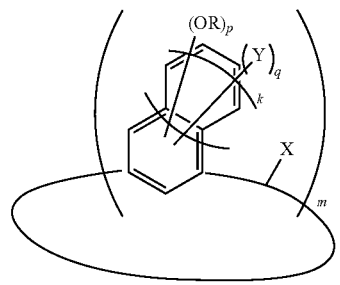

(3)

wherein in the formula (3), R represents a hydrogen atom or a monovalent organic group having 1 to 30 carbon atoms; m is an integer of 4 to 12; Y, k, p and q are as defined in the formula (1); and X is as defined in the case where j in the formula (2) is 1, wherein a plurality of Rs are identical or different, a plurality of Xs are identical or different, a plurality of "k"s are identical or different, a plurality of "p"s are identical or different, and a plurality of "q"s are identical or different, and wherein in a case where Y is present in a plurality of number, a plurality of Ys are identical or different.

Appendix 8

The composition for forming a resist underlayer film according to appendix 6, wherein the calixarene-based compound is represented by a formula (4),

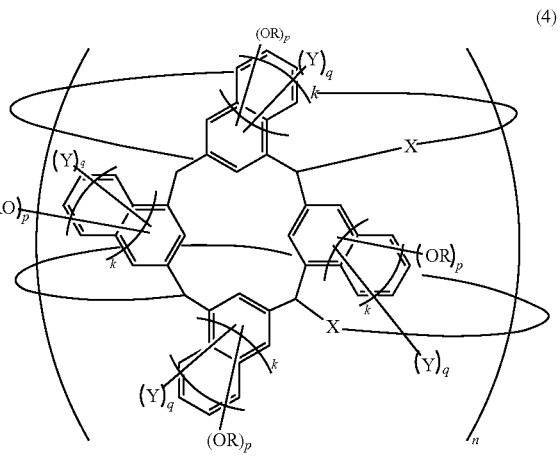

(4)

wherein in the formula (4), R represents a hydrogen atom or a monovalent organic group having 1 to 30 carbon atoms; n is 2 or 3; Y, k, p and q are as defined in the formula (1); and X is as defined in the case where j in the formula (2) is 2, wherein a plurality of Rs are identical or different, a plurality of Xs are identical or different, a plurality of "k"s are identical or different, a plurality of "p"s are identical or different, and a plurality of "q"s are identical or different, and wherein in a case where Y is present in a plurality of number, a plurality of Ys are identical or different.

Appendix 9

The composition for forming a resist underlayer film according to appendix 6, wherein the calixarene-based compound is represented by a formula (5),

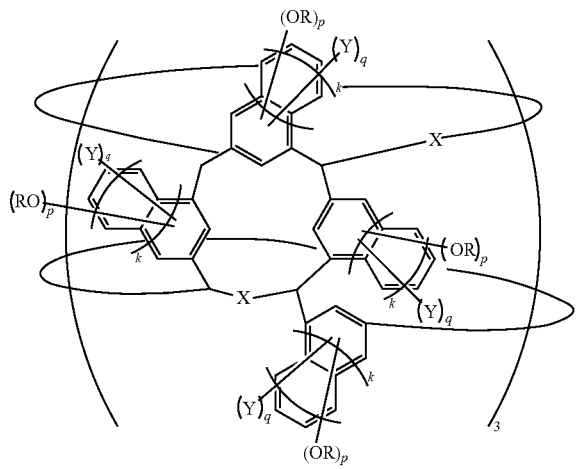

(5)

wherein in the formula (5), R represents a hydrogen atom or a monovalent organic group having 1 to 30 carbon atoms; Y, k, p and q are as defined in the formula (1); and X is as defined in the case where j in the formula (2) is 2, wherein a plurality of Rs are identical or different, a plurality of Xs are identical or different, a plurality of "k"s are identical or different, a plurality of "p"s are identical or different, and a plurality of "q"s are identical or different, and wherein in a case where Y is present in a plurality of number, a plurality of Ys are identical or different.

Appendix 10

The composition for forming a resist underlayer film according to appendix 1, wherein a molecular weight of the calixarene-based compound is no less than 500 and no greater than 3,000.

Appendix 11

The composition for forming a resist underlayer film according to appendix 1, wherein the organic solvent comprises a polyhydric alcohol partial ether acetate solvent, a ketone solvent, a carboxylic acid ester solvent, or a mixed solvent thereof.

Appendix 12

The composition for forming a resist underlayer film according to appendix 1, further comprising a resin other than resins corresponding to the calixarene-based compound.

Appendix 13

The composition for forming a resist underlayer film according to appendix 12, wherein the resin comprises a crosslinkable group.

Appendix 14

The composition for forming a resist underlayer film according to appendix 12, wherein the resin comprises a novolak resin, a resol resin, a styrene resin, an acenaphthylene resin, a polyarylene resin or a mixture thereof.

Appendix 15

The composition for forming a resist underlayer film according to appendix 12, wherein a weight average molecular weight of the resin is no less than 2,000 and no greater than 8,000.

Appendix 16

The composition for forming a resist underlayer film according to appendix 12, wherein a content of the resin with respect to 100 parts by mass of the calixarene-based compound is no less than 5 parts by mass and no greater than 1,000 parts by mass.

Appendix 17

The composition for forming a resist underlayer film according to appendix 1, wherein the composition is for use on a substrate having a plurality of types of trenches.

Appendix 18

The composition for forming a resist underlayer film according to appendix 17, wherein the plurality of types of trenches differ from one another in terms of an aspect ratio.

Appendix 19

The composition for forming a resist underlayer film according to appendix 18, wherein a ratio of a maximum value to a minimum value of the aspect ratios of the plurality of types of trenches is no less than 10.

Appendix 20

A pattern-forming method comprising in a following order of:
providing a resist underlayer film directly or indirectly on a substrate; forming a resist pattern directly or indirectly on the resist underlayer film;
forming a pattern on the substrate through dry etching of the resist underlayer film, the substrate, or both the resist underlayer film and the substrate using the resist pattern as a mask; and
removing the resist underlayer film remaining on the substrate using a basic solution,
wherein the method further comprises subjecting the resist underlayer film to heating or an acid treatment before removing the resist underlayer film, and
wherein the resist underlayer film is provided using the composition for forming a resist underlayer film according to appendix 1.

Appendix 21

The pattern-forming method according to appendix 20, wherein the substrate is stepped.

Appendix 22

The pattern-forming method according to appendix 20, wherein the substrate comprises a plurality of types of trenches.

Appendix 23

The pattern-forming method according to appendix 22, wherein the plurality of types of trenches differ from one another in terms of an aspect ratio.

Appendix 24

The pattern-forming method according to appendix 23, wherein a ratio of a maximum value to a minimum value of the aspect ratios of the plurality of types of trenches is no less than 10.

Appendix 25

The pattern-forming method according to appendix 20, comprising after providing the resist underlayer film and before forming the resist pattern:
providing an intermediate layer directly or indirectly on the resist underlayer film,
wherein the intermediate layer is further dry etched in forming the substrate pattern.

Obviously, numerous modifications and variations of the present invention are possible in light of the above teachings. It is therefore to be understood that within the scope of the appended claims, the invention may be practiced otherwise than as specifically described herein.

The invention claimed is:

1. A composition comprising:
a calixarene-based compound obtained from a calixarene by substituting at least a part of hydrogen atoms on phenolic hydroxyl groups comprised in the calixarene, with a monovalent organic group, the monovalent organic group comprising 1 to 30 carbon atoms and a crosslinkable group; and
an organic solvent,
wherein the calixarene-based compound is represented by formula (4),

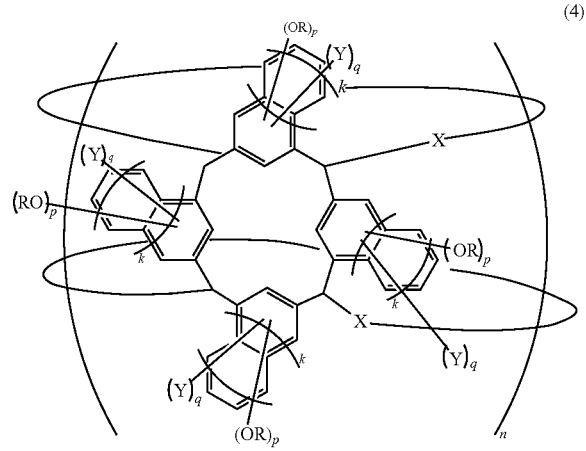

(4)

wherein in the formula (4), R represents a hydrogen atom, a monovalent organic group having 1 to 30 carbon atoms, or a monovalent organic group comprising 1 to 30 carbon atoms and a crosslinkable group; n is 2 or 3; Y represents a hydrocarbon group having 1 to 10 carbon atoms; q is an integer of 0 to 7; p is an integer of 1 to 3, wherein a sum of p and q is no less than 1 and no greater than 8; k is 0 or 1; and X represents a substituted or unsubstituted hydrocarbon group having 1 to 30 carbon atoms and a valency of 2, wherein a plurality of Rs are identical or different, a plurality of Xs are identical or different, a plurality of "k"s are identical or different, a plurality of "p"s are identical or different, and a plurality of "q"s are identical or different, and wherein in a case where Y is present in a plurality of number, a plurality of Ys are identical or different,
wherein in a case where R is the monovalent organic group comprising 1 to 30 carbon atoms and the crosslinkable group, the crosslinkable group is a group comprising a polymerizable carbon-carbon triple bond; an epoxy group; an alkoxymethyl group; a formyl group; an acetyl group; a dialkylaminomethyl group; a dimethylolaminomethyl group, a group represented by formula (a), a group represented by formula (b), or a group represented by formula (c):

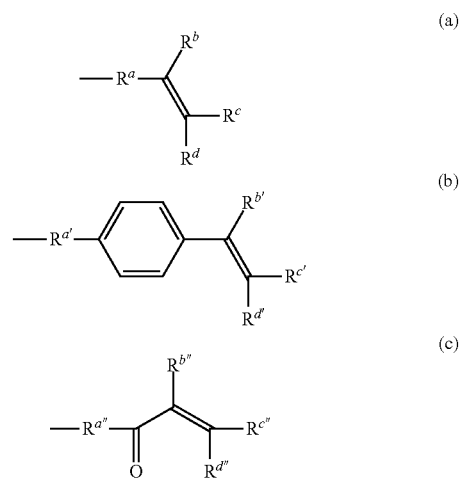

wherein $R^a$ and $R^{a'}$ each independently represent a single bond or an alkanediyl group having 1 to 10 carbon atoms; $R^{a''}$ represents a single bond, an alkanediyl group, a hydroxyalkanediyloxy group or $(R''O)_i$; R'' represents an alkanediyl group; "i" is an integer of 1 to 10; $R^{b''}$ represents a hydrogen atom; and $R^b$, $R^{b'}$, $R^c$, $R^{c'}$, $R^{c''}$, $R^d$, $R^{d'}$ and $R^{d''}$ each independently represent a hydrogen atom or a monovalent hydrocarbon group.

2. The composition according to claim 1, wherein a part of hydrogen atoms on phenolic hydroxyl groups of the calixarene-based compound is substituted.

3. The composition according to claim 2, wherein a ratio of the number of substituted phenolic hydroxyl groups to the number of unsubstituted phenolic hydroxyl groups in the calixarene-based compound is no less than 30/70 and no greater than 99/1.

4. The composition according to claim 1, wherein a molecular weight of the calixarene-based compound is no less than 500 and no greater than 3,000.

5. The composition according to claim 1, wherein the organic solvent comprises a polyhydric alcohol partial ether acetate solvent, a ketone solvent, a carboxylic acid ester solvent, or a mixed solvent thereof.

6. The composition according to claim 1, further comprising a resin other than a resin corresponding to the calixarene-based compound.

7. The composition according to claim 6, wherein the resin comprises a crosslinkable group.

8. The composition according to claim 6, wherein the resin comprises a novolak resin, a resol resin, a styrene resin, an acenaphthylene resin, a polyarylene resin or a mixture thereof.

9. The composition according to claim 6, wherein a weight average molecular weight of the resin is no less than 2,000 and no greater than 8,000.

10. The composition according to claim 6, wherein a content of the resin with respect to 100 parts by mass of the calixarene-based compound is no less than 5 parts by mass and no greater than 1,000 parts by mass.

11. A pattern-forming method comprising in a following order of:

applying the composition according to claim 1 directly or indirectly on a substrate to provide a resist underlayer film;

forming a resist pattern directly or indirectly on the resist underlayer film;

forming a pattern on the substrate through dry etching of the resist underlayer film, the substrate, or both the resist underlayer film and the substrate using the resist pattern as a mask; and removing the resist underlayer film remaining on the substrate using a basic solution, wherein the method further comprises subjecting the resist underlayer film to heating or an acid treatment before removing the resist underlayer film.

12. The pattern-forming method according to claim 11, wherein the substrate is stepped.

13. The pattern-forming method according to claim 11, wherein the substrate comprises a plurality of kinds of trenches.

14. The pattern-forming method according to claim 13, wherein the plurality of kinds of trenches differ from one another in terms of an aspect ratio.

15. The pattern-forming method according to claim 14, wherein a ratio of a maximum value of the aspect ratio to a minimum value of the aspect ratio of the plurality of kinds of trenches is no less than 10.

16. The pattern-forming method according to claim 11, further comprising after providing the resist underlayer film and before forming the resist pattern:

providing an intermediate layer directly or indirectly on the resist underlayer film, wherein the intermediate layer is further dry etched in forming the substrate pattern.

* * * * *